(12) United States Patent
Zhang et al.

(10) Patent No.: US 10,752,945 B2
(45) Date of Patent: Aug. 25, 2020

(54) ACCURATE GENOME SEQUENCING OF SINGLE CELLS BY SINGLE-STRANDED AMPLIFICATION AND SEQUENCING

(71) Applicant: The Regents of the University of California, Oakland, CA (US)

(72) Inventors: Kun Zhang, San Diego, CA (US); Xiaohua Huang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 615 days.

(21) Appl. No.: 14/427,163

(22) PCT Filed: Sep. 10, 2013

(86) PCT No.: PCT/US2013/059086
§ 371 (c)(1),
(2) Date: Mar. 10, 2015

(87) PCT Pub. No.: WO2014/043140
PCT Pub. Date: Mar. 20, 2014

(65) Prior Publication Data
US 2015/0247191 A1    Sep. 3, 2015

Related U.S. Application Data

(60) Provisional application No. 61/700,276, filed on Sep. 12, 2012.

(51) Int. Cl.
*C12Q 1/68*    (2018.01)
*C12Q 1/6869*  (2018.01)
*B01L 3/00*    (2006.01)

(52) U.S. Cl.
CPC .......... *C12Q 1/6869* (2013.01); *B01L 3/5027* (2013.01); *B01L 2200/10* (2013.01)

(58) Field of Classification Search
None
See application file for complete search history.

(56) References Cited

U.S. PATENT DOCUMENTS

| 6,323,009 | B1 | 11/2001 | Lasken et al. |
| 8,097,405 | B1 | 1/2012 | Engelhardt et al. |
| 8,137,912 | B2 | 3/2012 | Kapur et al. |
| 2004/0110208 | A1 | 6/2004 | Chan et al. |
| 2004/0185484 | A1 | 9/2004 | Costa et al. |
| 2004/0209298 | A1 | 10/2004 | Kamberov et al. |

(Continued)

FOREIGN PATENT DOCUMENTS

| CN | 102212614 | 10/2011 |
| EP | 0675966 | 10/2004 |

(Continued)

OTHER PUBLICATIONS

Fan, CH., et al. Whole-genome molecular haplotyping of single cells. Nature Biotechnology, vol. 29 (1), p. 51-57, Jan. 2011.*

(Continued)

*Primary Examiner* — Aaron A Priest
(74) *Attorney, Agent, or Firm* — Knobbe, Martens, Olson & Bear, LLP

(57) ABSTRACT

Methods and devices for accurate genome sequencing, including sequencing of single cells by single-stranded amplification and sequencing are provided herein.

13 Claims, 10 Drawing Sheets

(56) References Cited

U.S. PATENT DOCUMENTS

| | | | |
|---|---|---|---|
| 2006/0014167 | A1 | 1/2006 | Church et al. |
| 2008/0014589 | A1 | 1/2008 | Link et al. |
| 2008/0138809 | A1* | 6/2008 | Kapur .............. G01N 33/6893 435/6.11 |
| 2011/0039303 | A1* | 2/2011 | Jovanovich ......... F16K 99/0001 435/91.2 |
| 2012/0115736 | A1 | 5/2012 | Bjornson et al. |
| 2012/0196754 | A1* | 8/2012 | Quake .................. C12Q 1/6806 506/2 |
| 2014/0378350 | A1* | 12/2014 | Hindson ............ C12N 15/1065 506/26 |
| 2015/0133310 | A1* | 5/2015 | Hayden ............... C12Q 1/6806 506/2 |

FOREIGN PATENT DOCUMENTS

| | | |
|---|---|---|
| JP | 2004-313112 | 11/2004 |
| WO | WO 94/18218 | 8/1994 |
| WO | WO 00/40750 | 7/2000 |
| WO | WO 00/53812 | 9/2000 |
| WO | WO 2011/050981 | 5/2011 |
| WO | WO 2012/089148 | 7/2012 |
| WO | WO-2012113072 A1 * 8/2012 ........... C12Q 1/6811 |

OTHER PUBLICATIONS

Marcy, Y. et al. Nanoliter reactors improve multiple strand displacement amplification of genomes from single cells. Plos Genetics, vol. 3(9), e155, p. 1702-1708, 2007.*

Bhat et al., Effect of sustained elevated temperature prior to amplification on template copy number estimation using digital polymerase chain reaction, Analyst. Feb. 21, 2011;136(4):724-32. doi: 10.1039/c0an00484g. Epub Nov. 25, 2010.*

Office Action dated Jun. 9, 2017 in Chinese App. No. 201380055254.7, with machine translation.

Office Action dated Jun. 16, 2017 in EP App. No. 13 837 591.0.

Albertini, R.J., Nickles, J.A., O'Neill, J.P. and Robison, S.H. (1990). In vivo somatic mutations in humans: measurement and analysis. Annu Rev Genet 24, 305-326.

Baslan, T., Kendall, J., Rodgers, L., Cox, H., Riggs, M., Stepansky, A., Troge, J., Raavl, K., Esposito, D., Lakshmi, B., et al. (2012). Genome-wide copy number analysis of single cells. Nat Protoc 7, 1024-1041.

European Supplementary Search Report dated Mar. 31, 2016 in Application No. 13837591.0.

Fan et al. Nature Biotechnology, 2011. 29:51-57.

Garcia, A.M., Busuttil, R.A., Rodriguez, A., Cabrera, C., Lundell, M., Dolle, M.E., and Vljg, J. (2007). Detection and analysis of somatic mutations at 1acZ reporter locus in higher organizms: application to Mus musculus and *Drosophilia melanogaster*, Methods Mol Biol 371, 267-287.

Gore, A., Li, Z., Fung, H.L, Young, J.E., Agarwal, S,. Antosiewicz-Bourget, J., Canto, I., Giorgetti, A., Israel, M.A., Kiskinis, E., et al. (2011). Somatic coding mutations in human induced pluripotent stem cells. Nature 471, 63-67.

Hou, Y., Song, L., Zhu, P., Zhang, B., Tao, Y., Xu, X., Li, F., Wu, K., Liang, J., Shao, D., et al. (2012). Single-cell exome sequencing and monoclonal evolution of a JAK2-negative myeloproliferative neoplasm. Cell 148, 873-885.

International Preliminary Report on Patentability dated Sep. 12, 2012 in Application No. PCT/US2013/059086.

International Search Report and Written Opinion dated Dec. 2, 2013 in Application No. PCT/US2013/059086.

Israel, M.A., Yuan, S.H., Bardy, C., Reyna, S.M., Mu, Y., Herrera, C., herreran, M.P., Van Gorp, S., Nazor, K.L., Boscolo, F.S., et al. (2012). Probing sporadic and familial Alzheimer's disease using induced pluripotent stem cells. Nature 482, 216-220.

Luria, S.F. and Delbruck, M. (1943). Mutations of Bacteria from Virus Sensitivity to Virus Resistance. Genetics 28, 491-511.

Marcy Y., Ishoey T., Lasken RS, Stockwell TB, Walenz BP, Halpern AL, Beeson KY, Goldberg SM, Quake SR (2007). Nanoliter reactors improve multiple displacement amplification of genomes from single cells. PLos Genet 3, 1702-1708.

Muotri, A.R., and Gage, F.H. (2006). Generation of neuronal variability and complexity. Nature 441, 1087-1093.

Office Action dated Mar. 16, 2016 in Chinese Application No. 201380055254.7 with summary English Translation.

Navin, N., Kendall, J., Troge, J., Andrews, P., Rodgers, L., McIndoo, J., Cook, K., Stepansky, A., Lefy, D., Esposito, D., et al. (2011). Tumour evolution inferred by single-cell sequencing. Nature 472, 90-94.

Rehen, S.K., Yung, Y.C., McCreight, M.P., Kaushal, D., Yang, A.H., Almeida, B.S., Kingsbury, M.A., Cabral, K.M., McConnell, M.J., Anliker, B., et al. (2005). Constitutional aneuploidy in the normal human brain. J Neurosci 25, 2176-2180.

Rehen, S.K., McConnell, M.J., Kaushal, D., Kingsbury, M.A., Yang, A.H., and Chung, J. (2001). Chromosomal variation in neurons of the developing and adult mamallian nervous system. Proc Natl acad Sci USA 98, 13361-13366.

Roach, J.C., Glusman, G., Smit, A.F., Huff, C.D., Hubley, R., Shannon, P.T., Rowen, L., Pant, K.P., Goodman, N., Bamshad, M., et al. (2010). Analysis of genetic inheritance in a family quartet by whole-genome sequencing. Science 328, 636-639.

Schmitt et al., "Detection of ultra-rare mutations by next-generation sequencing", Proceedings of the National Academy of Sciences, vol. 109, No. 36, Aug. 1, 2012, pp. 14508-14513.

Singer, T., McConnell, M.J., Marchetto, M.C., Coufal, N.G., and Gage, F.H. (2010). LINE-1 retrotransposons: mediators of somatic variation in neuronal genomes? Trends Neurosci 33, 345-354.

Westra, J.W., Rivera, R.R., Bushman, O.M., Yung, Y.C., Peterson, S.E., Barral, S., and Chun, J. (2010). Neronal DNA content variation (DCV) with regional and individual differences in the human brain. J Comp Neurol 518, 3981-4000.

Xu X, Hou Y, Yin X, Bao L, Tang A, Song L, Li F, Tsang S, Wu K, Wu H et al. 2012. Single-cell exome sequencing reveals single-nucleotide mutation characteristics of a kidney tumor. Cell 148: 886-895.

Yang, A.H., Kaushal, D., Rehen, S.K., Krledt, K., Kingsbury, M.A., McConnell, M.J., and Chun, J. (2003). Chromosome segregation defects contribute to aneuploidy in normal neural progenitor cells. J Neurosci 23, 10454-10462.

Yuan, S.H., Martin, J., Elia, J., Flippin, J., Paramban, R.I., Hefferan, M.P., Vidal, J.G., Mu, Y., Killian, R.L., Israel, M.A., et al. (2011). Cell-surface marker signatures for the isolation of neural stem cells, glia and neruons derived from human pluripotent stem cells. PLos One 6, e17540.

Yurov, Y.B., Iourov, I.Y., Vorsanova, S.G., Liehr, T., Kolotil, A.D., Kutsev, S.I., Pellestor, F., Beresheva, A.K., Demidova, I.A., Kravets, V.S., et al, (2007), Aneuploidy and confined chromosomal mosaicism in the developming human brain. Plos One 2, e558.

Zhang K., Martiny A.C., Reppas N.B., Barry K.W., Malek J., Chisholm S.W., Church G.M. (2006) Sequencing genomes from single cells by polymerase cloning. Nature Biotechnology 24:880-686.

Office Action dated Dec. 11, 2017 in Chinese Application No. 201380055254.7 with English Translation.

Office Action dated Feb. 16, 2018 in European Application No. 13837591.0.

Roche, "Process Steps Overview", accessible on the world wide web at https://www.reed.edu/biology/professors/srenn/pages/teaching/BIO431S05_2008/431S05_readings/Week_2/Keller_20080208.html/Roche_KBantle.ppt, 37 pages, This item was accessed on Jul. 13, 2018, This lists a date created as Nov. 29, 2004, and lists copyright dates of 1996-2012. However, as this item was accessible on the world wide web, it may have been available in some form at an earlier pornt in time.

Office Action dated Oct. 24, 2018 in European Application No. 13 837 591.0

Office Action dated Sep. 5, 2018 in Chinese Application No. 201380055254.7.

(56) References Cited

OTHER PUBLICATIONS

Margulies et al., "Genome sequencing in microfabricated high-density picolitre reactors", Nature, vol. 437, pp. 376-380, Sep. 15, 2005.

Margulies et al., Supplementary Materials and Methods section of "Genome sequencing in microfabricated high-density picolitre reactors", Nature, vol. 437, 34 pages, Sep. 15, 2005, Manuscript 2005-05-05204.

\* cited by examiner

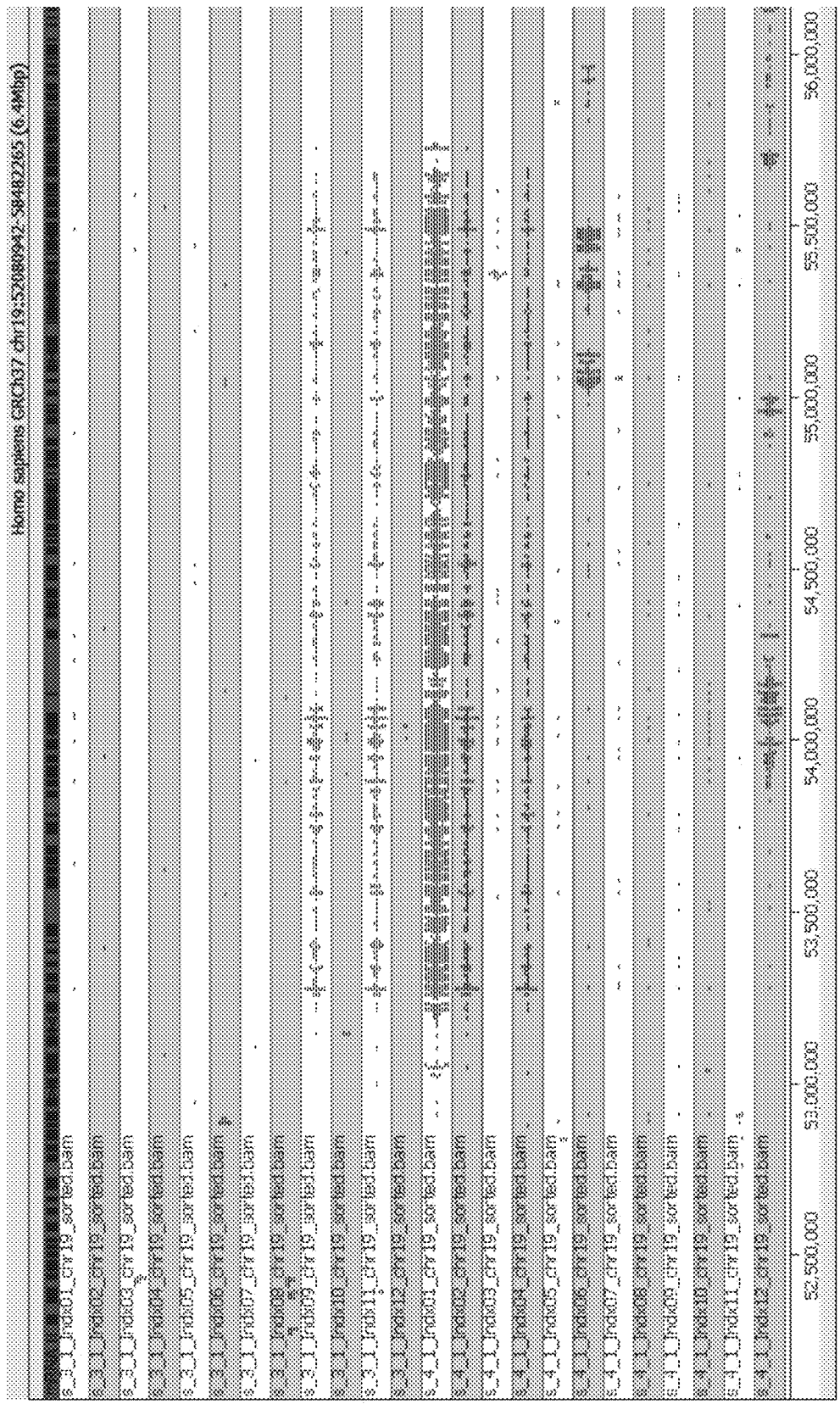
FIG 3¹

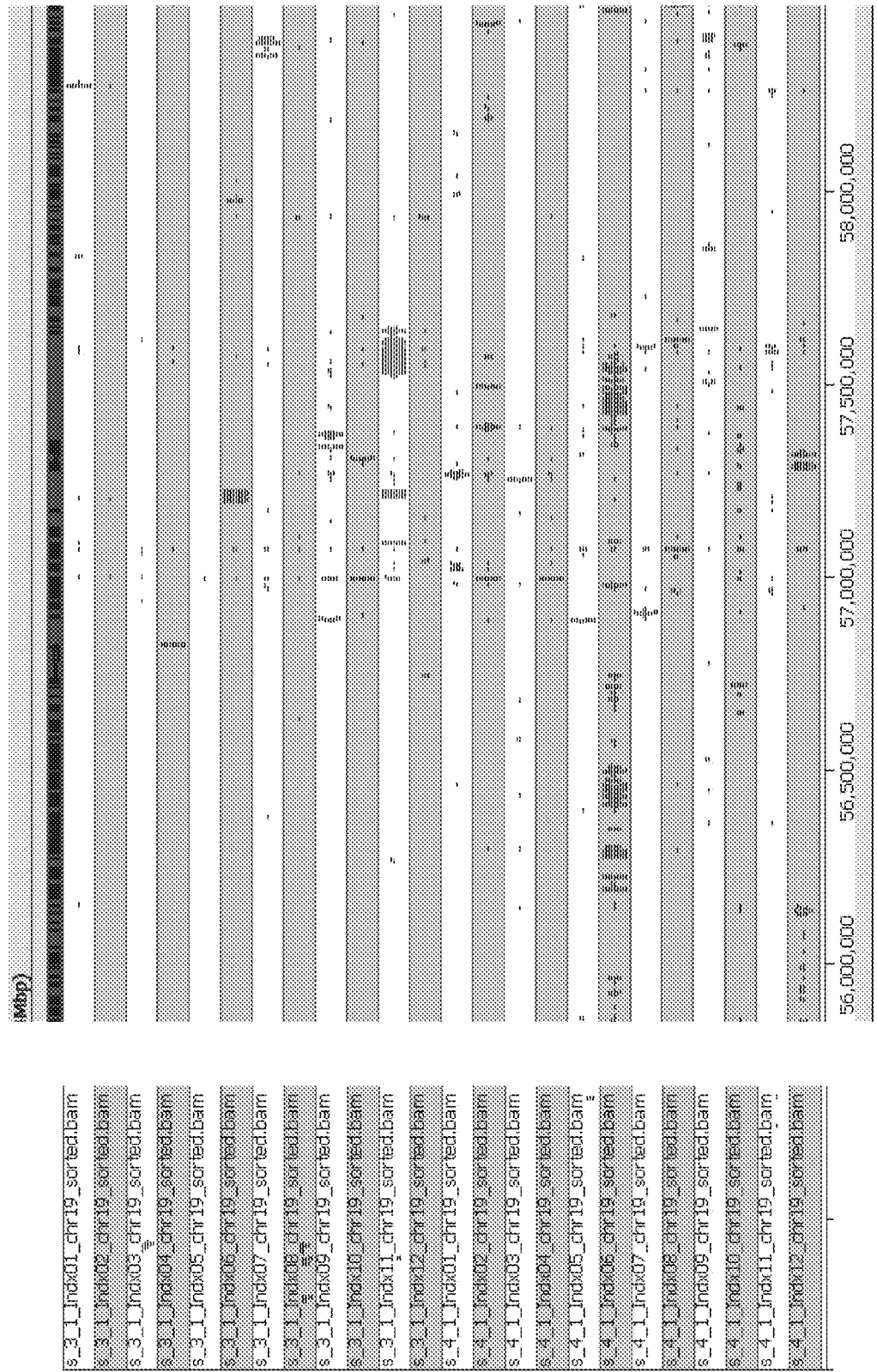
FIG 3²

ACCURATE GENOME SEQUENCING OF SINGLE CELLS BY SINGLE-STRANDED AMPLIFICATION AND SEQUENCING

CROSS-REFERENCE TO RELATED APPLICATIONS

This application is the national phase of PCT Application No. PCT/US2013/059086, filed Sep. 10, 2013, which claims the benefit of U.S. Provisional Application No. 61/700,276, filed Sep. 12, 2012, the entirety of which is incorporated by reference herein.

STATEMENT REGARDING FEDERALLY SPONSORED R&D

This invention was made with government support under GM 097253 and HG005550 awarded by the National Institutes of Health. The government has certain rights in the invention.

FIELD

Embodiments herein relate generally to methods and devices for sequencing genomic nucleic acids, including sequencing genomic nucleic acids of a single cell.

BACKGROUND

Indirect measurement of mutation rate was pioneered by Luria and Delbruck in their classic Fluctuation Test (Luria and Delbruck 1943). The concept of measuring somatic mutation by quantifying the number of cells that show phenotypic changes was extended to human cells, using genes such as HLA, HPRT or TK. Albertini et al. 1990, the disclosure of which is incorporated by reference in its entirety herein. A lacZ reporter assay was developed for model organisms such as mouse or fly of which transgenic progenies can be made (Garcia et al. 2007, the disclosure of which is incorporated by reference in its entirety herein). Such indirect assays typically assume a constant level of penetrance for mutations, which can be problematic. In addition, the indirect measurement of mutation rate in a kilobase-size locus is extrapolated to the entire genome, based on an oversimplified assumption of constant mutation rate throughout the genome. These limitations call for direct measurements of mutation rate in human cells genome-wide. The germline mutation rate in human was directly measured very recently (Roach et al. 2010, the disclosure of which is incorporated by reference in its entirety herein), yet direct measuring of somatic mutation rate genome-wide remains to be demonstrated almost 80 years after the Luria-Delbruck experiment.

Rapid advances in DNA sequencing technology have made it possible for routine de novo sequencing of many organisms, and re-sequencing of human individuals or human cancers. Single cell sequencing experiments have been described in Marcy et al. 2007 and Fan et al. Nature Biotechnology, 2011, 29:51-57, the disclosure of which is incorporated by reference in its entirety herein.

SUMMARY

Some aspects of the invention include methods of sequencing a genomic nucleic acid in a single cell is provided. The methods can include isolating a plurality of double-stranded nucleic acids of a single cell, in which each double-stranded nucleic acid of the plurality comprises a first strand of nucleic acid and a second strand of nucleic acid, and in which the first strand of nucleic acid and the second strand of nucleic acid are complementary to each other; separating the first strand of nucleic acid from the second strand of nucleic acid of each double-stranded nucleic acid of the plurality of double-stranded nucleic acids; placing the first strands and second strands of the plurality of double-stranded nucleic acids in a plurality of solutions, in which each of the plurality of solutions is separate from each other solution, and in which the number of strands in each solution is substantially similar; and sequencing each strand. In some embodiments, the double-stranded nucleic acids comprise parts of a chromosome. In some embodiments, the double-stranded nucleic acids comprise parts of a chromosome fragment. In some embodiments, each of the plurality of solutions has a volume of about 10 nl or less. In some embodiments, each of the plurality of solutions has a volume of about 4 nl or less. In some embodiments, each of the plurality of solutions has a volume of about 2 nl or less. In some embodiments, each of the plurality of solutions has a volume of about 1 nl or less. In some embodiments, each of the plurality of solutions has a volume of about 0.4 nl or less. In some aspects of these embodiments, sequencing comprises error rate of less than about 1 in $10^{12}$. In some aspects of these embodiments, sequencing comprises an error rate of less than about 1 in $10^{10}$. In some embodiments, the method comprises amplifying each strand. In some embodiments, each strand is amplified in one of the plurality of solutions prior to sequencing. In some embodiments, amplifying each strand comprises multiple displacement amplification. In some embodiments, each strand is amplified to a magnitude of no more than about 10,000-fold. In some embodiments, each strand is amplified to a magnitude of no more than about 1,000-fold. In some embodiments, each strand is amplified for no more than about 24 hours. In some embodiments, each strand is amplified for no more than about 10 hours. In some embodiments, each strand is amplified for no more than about 5 hours. In some embodiments, the plurality of solutions comprises at least about 48 solutions. In some embodiments, the plurality of solutions comprises at least about 24 solutions. In some embodiments, the plurality of solutions is positioned in a microfluidic device. In some embodiments, the microfluidic device is as described herein. In some embodiments, a probability that a first strand and a second strand of a double-stranded nucleic acid are in separate solution environments is at least 95%. In some embodiments, the probability is at least 98%. In some embodiments, the nucleic acid comprises DNA. In some embodiments, the single cell comprises a neuron.

Some aspects of the invention include a microfluidic device for sequencing nucleic acids, the device comprising: a microfluidic device for sequencing nucleic acids, the device comprising: a single-cell capture module; a member configured for cell lysis and nucleic strand partitioning; and a plurality of chambers. The single-cell capture module can be in fluid communication with the member, and wherein the member is in fluid communication with the plurality of reaction chambers. The device can be configured to distribute a plurality of partitioned single-stranded nucleic acids substantially evenly among the plurality of chambers. In some embodiments, the member comprises a rotary member. In some embodiments, the member comprises a passive diffusion membrane. In some embodiments, the double-stranded nucleic acids comprise portions of chromosomes. In some embodiments, the double-stranded nucleic acids comprise portions of chromosome fragments. In some embodiments, each of the plurality of chambers has a volume of about 10 nl or less. In some embodiments, each of the plurality of chambers has a volume of about 4 nl or less. In some embodiments, each of the plurality of chambers has a volume of about 2 nl or less. In some embodiments, each of the plurality of chambers has a volume of about 1 nl or less. In some embodiments, each of the plurality of chambers has a volume of about 0.4 nl or less. In some embodiments, an inner surface of the device is coated with a non-stick polymer. In some embodiments, the non-stick polymer comprises PEG. In some embodiments, the plurality of chambers comprises at least about 24 chambers. In some embodiments, the plurality of chambers comprises at least about 48 chambers. In some embodiments, each of the plurality of chambers is configured for multiple-displacement amplification. In some embodiments, the microfluidic device is configured to automatically capture a single cell, lyse the cell, and substantially evenly distribute single-stranded nucleic acids of the cell to the plurality of chambers. In some embodiments, each of the plurality of chambers is configured to transfer a quantity of fluid to a reaction vessel for sequencing library preparation

BRIEF DESCRIPTION OF THE DRAWINGS

FIG. 3 is a diagram illustrating sequencing of a representative single 2.5 Mb fragment of *Homo sapiens* chromosome 19 according to some embodiments herein. The chromosomes of the entire *H. sapiens* were separated, uniformly amplified and sequenced according to methods of some embodiments herein. It is noted that FIG. 3 includes two panels, FIG. $3^1$, representing the left side of the diagram and FIG. $3^2$ representing the right side.

DETAILED DESCRIPTION

Figure 1A:
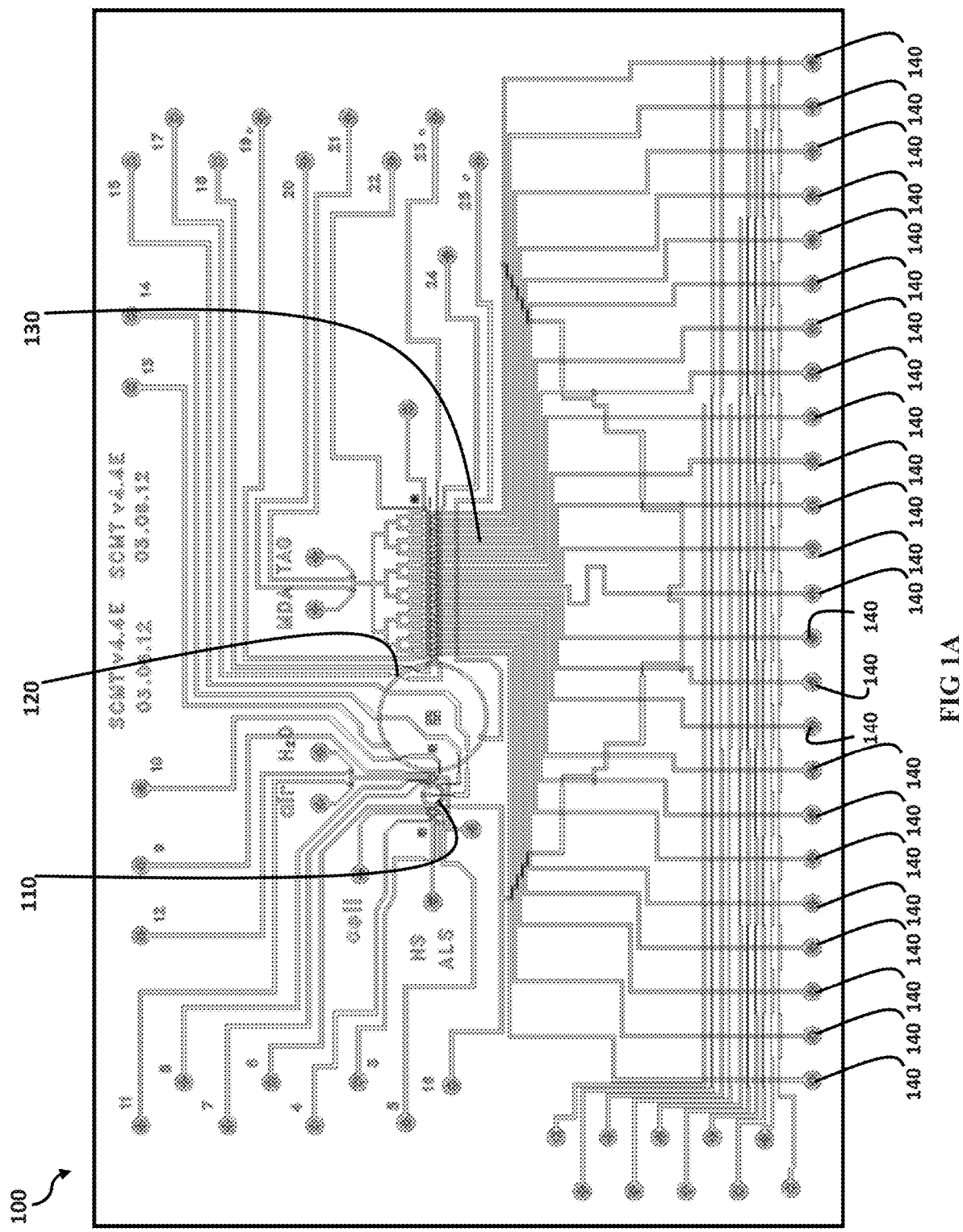
FIG. 1A is a schematic diagram of a microfluidic chip according to some embodiments herein.

Some embodiments include a technology referred to herein as SISSOR (SIngle-Stranded Sequencing using micrOfluidic Reactors) for accurate genome sequencing of single mammalian cells. The two complementary strands of double-stranded nucleic acid molecules in a single cell can be separated for independent amplification and sequencing, and the redundant sequencing data from the Watson and Crick strands can used to distinguish dozens of true mutations per genome from sequencing errors, which can potentially number in the thousands to tens of thousands. In some embodiments, the accuracy rate of SISSOR is greater than 10,000-fold higher than existing methods. Some embodiments include implementation of SISSOR via a microfluidic device to perform three major functions: (1) single cell capture, (2) lysis and single-strand DNA partitioning, and (3) single-molecule whole genome amplification.

Sequencing the mammalian-size genome in a single cell at the accuracy sufficient for detecting rare somatic point mutations can be a major challenge. Such sequencing was previously extremely difficult because: (i) the mammalian genome is large ($\sim 10^9$ bps) whereas the somatic mutation rate is very low ($\sim 10^{-9}$ by per cell division), necessitating a method with extremely low false positive rate) ($\sim 10^{-10}$); (ii) in vitro amplification of DNA from single cells has an error rate of $10^{-6}$ or 1,000-time higher than the mutation rate, which is the Achilles' heel for single-cell sequencing: false positives generated by polymerase errors alone greatly outnumber the true mutations.

A number of studies on single-cell sequencing of cancers were reported recently, which have generated great excitement in the community. However, these existing methods can only detect either gain or loss of large chromosomal regions (Navin et al. 2011), or single-nucleotide changes at the error rate of $10^{-5}$ (Hou et al. 2012; Xu et al. 2012). Cancer genomes also represent a lower hanging fruit due to the higher mutation rate and hence a lower requirement in sequencing errors. For a limited number of somatic cell types, one can derive clonal populations from diluted single cells for routine sequencing. However, clonal expansion in vitro might introduce additional mutations and lead to an over-estimation of mutation rate, as was observed in a recent study (Gore et al. 2011). A direct measurement of somatic mutation rate in the majority of human cell types after one cell division, would involve improving the accuracy by ~100,000-fold over these existing methods.

The idea of separating two complementary strands in a single cell for accurate sequencing is not trivial to implement. Every single DNA molecule in a cell would get all the way into the sequencer and produce usable data for error correction. To the best of Applicants' knowledge, all previous whole genome amplification methods have high amplification bias, such that even if the two DNA strands are separated, these previous methods will not obtain sequencing data from both stands for error identification. Despite numerous efforts on improving whole genome amplification methods in the past decade, until the present disclosure, amplification bias has been a major issue in single-cell whole genome amplification. In addition to biased amplification, DNA fragments can also bind nonspecifically to various surfaces (pipette tips, PCR tubes etc), and get lost. Loss of nucleic acid molecules represents another challenge when there is only one template molecule to start with.

In a recent study on somatic mutations in human induced embryonic stem cells, it was found that at least half of the mutations pre-exist in the somatic progenitor cells at various level of frequencies, some as low as five in 10,000 cells (Gore et al. (2011) Nature 471: 63-67). One following hypothesis is that every single cell in a somatic cell population carries a large number of private mutations, and these mutations become fixed (with or without selection) after reprogramming and clonal expansion. To test this hypothesis we can directly sequence individual progenitor cells and identify somatic mutations that occur at the frequency of $10^{-8}$ or lower, which is not believed to be possible with any existing technology.

Another line of observations is that mammalian brain is mosaic in terms of the nuclear genome of the neurons, which is due to at least three mechanisms: aneuploidy, LINE-1 retrotransposons and other DNA content variation. Furthermore, Jerold Chun's group at TSRI found evidence that somatic genomic changes of neurons in specific cortex areas correlate with a number of brain disorders, including Alzheimer's Disease and Autism Spectrum Disorders. Despite all the excitement generated by these observations, a full characterization of the extent of genomic diversity in individual neurons was previously not believed to be possible due to the same technical limitations with sequencing single cells.

In some embodiments, methods and microfluidic devices are provided which offer high accuracy (error rate~$10^{-10}$), single-nucleotide resolution, long-range haplotype information, no clonal expansion of diluted single cells is required, uniformly unbiased DNA amplification, and the option to be automated.

The methods and microfluidic devices according to some embodiments herein can be used for a variety of applications, including, but not limited to, early detection of rare mutations in cancers, direct detection of rare genomic mutations in single somatic cells, prenatal genetic diagnosis, and other genetic diagnostics that involve limited DNA input and high accuracy rate.

Sequencing according to some embodiments herein can allow for genome sequencing of single cells at an accuracy >10,000-fold higher than previous methods. Some embodiments take advantage of the redundant genetic information encoded in the Watson and Crick strands of single double-stranded nucleic acids (for example, in chromosomes) to overcome the issue of in vitro amplification error. A strand and its complementary strand can each be sequenced, and the sequences of the two strands can be compared. If there is a discrepancy between the determined sequences of the two strands, the discrepancy is much more likely to represent an in vitro sequencing error than a true mutation. In some embodiments, the sequences of the strands are compared to a reference sequence. If both sequences strands are consistent with each other, but differ from the reference sequence, the strands most likely contain a mutation or a variation relative to the reference sequence. Exemplary mutations or variations include, but are not limited to, single nucleotide polymorphisms (SNPs), deletions, insertions, duplications, and inversions. In some embodiments, the reference sequence is from a different cell of the same organism. In some embodiments, the reference sequence is from a cell of a different, related organism (for example, an organism of the same species, or an organism of a phylogenetically related species).

In some embodiments, a technology that allows sequencing of the genome of single mammalian cells at the consensus error rate of ~$10^{-10}$ in order to directly measure somatic mutations on single human cells is provided.

To this end, in some embodiments SISSOR (SIngle-Stranded Sequencing using micrOfluidic Reactors) is provided. SISSOR can take advantage of the redundant genetic information encoded in the Watson and Crick strands of a single cell to overcome the issue of in vitro amplification error. SISSOR can include separating the two complementary strands of double-stranded nucleic acid molecules in a single cell for independent amplification and sequencing, and use the redundant sequencing data from the Watson and Crick strands to distinguish dozens of true mutations per genome from thousands to tens of thousands of sequencing errors. Theoretically, in SISSOR according to some embodiments herein, one can achieve an error rate of $10^{-12}$, when two complementary strands of DNA are amplified in vitro separately at an error rate of $10^{-6}$, and the mutations are called only when sequencing data from the two strands are consistent. An error rate of $10^{-10}$ can be achievable according to some embodiments herein, given additional error sources, including chimeric sequences, hardware noise of the sequencing instrument, and computation mapping errors. The concept of obtaining sequence information from both the Watson and Crick strands of a DNA molecule was commonly used in the Sanger sequencing of bacterial clones, such as the generation of human reference genome in the Human Genome Project. Very recently, a related concept was applied to the improvement of accuracy for the second-generation sequencing technologies (Schmitt et al. 2012). However, to the best of Applicants' knowledge, embodiments herein represent the first implementation of single-strand sequencing on single cells, based on an innovative microfluidic platform.

Methods of Sequencing

According to some embodiments, methods of sequencing a double-stranded nucleic acid from a single cell are provided. The method can comprise isolating a plurality of double-stranded nucleic acids from the cell, separating the strands of the double-stranded nucleic acid. The method can comprise placing the strands in a plurality of solutions, in which each of the plurality of solutions is separate from each other solution, in which each of the plurality of solutions has a volume of about 4 nl or less, and in which the number of strands in each solution is substantially similar. The method can include sequencing the strands.

A variety of double-stranded nucleic acids can be used in accordance with embodiments herein, for example DNA, RNA, or DNA-RNA hybrids. Exemplary double-stranded nucleic acids that can be used in accordance with embodiments herein include chromosomes, minisomes, episomes, plasmids, or fragments of any of the listed items. While chromosomes are discussed in several exemplary embodiments herein, the skilled artisan will readily recognize that other double-stranded polynucleotides can be used in accordance with methods and compositions discloses herein. In some embodiments, the fragment has a length of at least about 100 kilobases, for example about 100 kilobases, 200, 300, 400, 500, 600, 700, 800, 900, 1000, 2000, 3000, 4000, 5000, 6000, 7000, 8000, 9000, 10,000, 20,000, 30,000, or 40,000 kilobases.

A variety of types of single cells can be used in accordance with embodiments herein, for example neurons, glial cells, germ cells, gametes, embryonic stem cells, pluripotent stem cells (including induced pluripotent stem cells), adult stem cells, cells of the hematopoietic lineage, differentiated somatic cells of a multicellular organism, microbial cells, cancer cells (including, for example cancer stem cells), disease cells, and the like.

Figure 4:
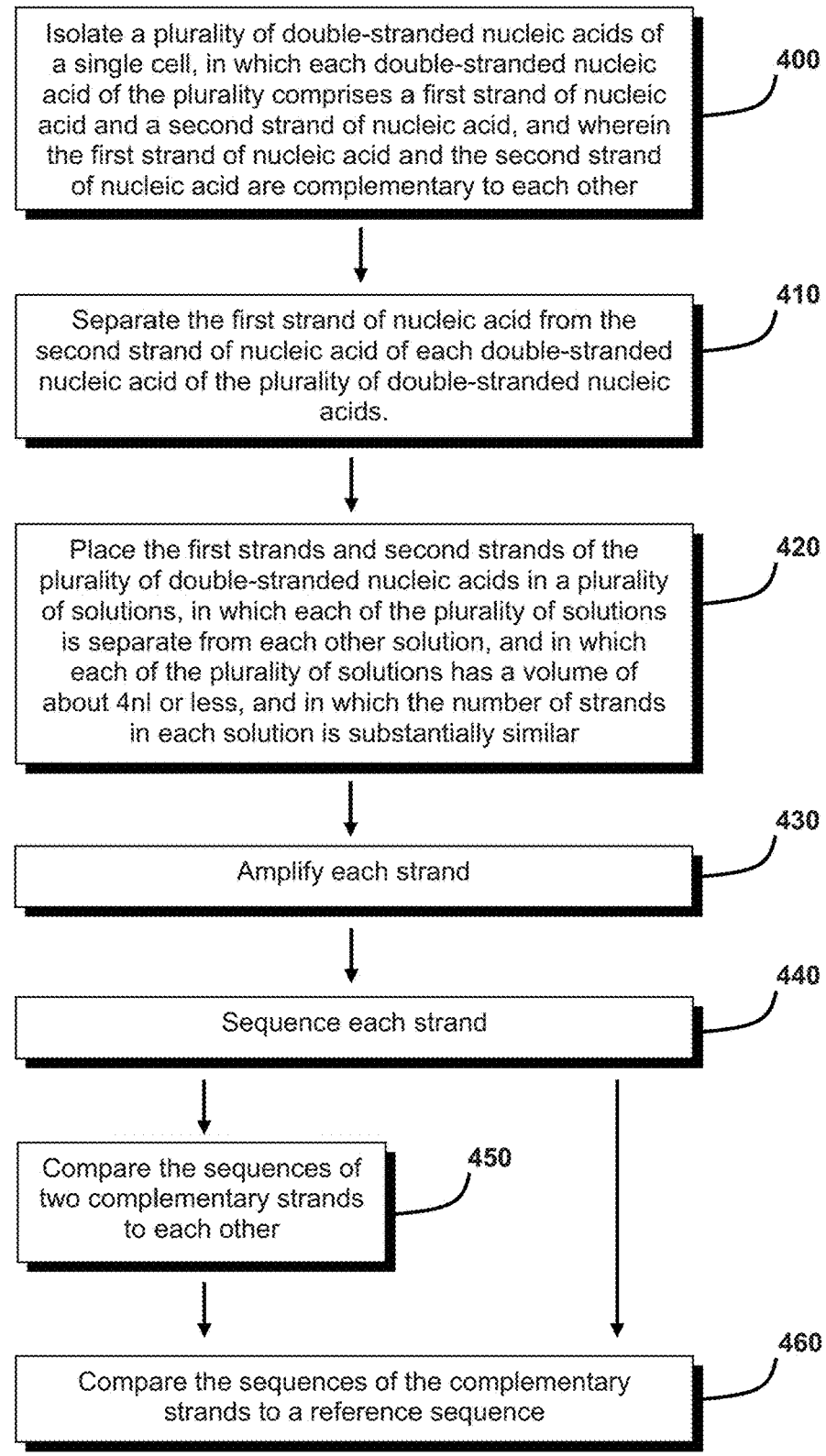
FIG. 4 is a flow diagram illustrating a method of sequencing a double-stranded nucleic acid of a single cell according to some embodiments herein.

FIG. 4 is a flow diagram illustrating methods of sequencing a double-stranded nucleic acid of a single cell according to some embodiments herein. The method can include isolating a plurality of double-stranded nucleic acids of a single cell, in which each double-stranded nucleic acid of the plurality can comprise a first strand of nucleic acid and a second strand of nucleic acid, and the first strand of nucleic acid and the second strand of nucleic acid can be complementary to each other 400. The method can include separating the first strand of nucleic acid from the second strand of nucleic acid of each double-stranded nucleic acid of the plurality of double-stranded nucleic acids 410. The method can include placing the first strands and second strands of the plurality of chromosomes in a plurality of solutions, in which each of the plurality of solutions is separate from each other solution, and in which each of the plurality of solutions has a volume of about 4 nl or less, and in which the number of strands in each solution is substantially similar 420. The method can include amplifying each strand 430. In some embodiments, each strand is amplified by no more than about 10,000-fold, for example no more than about 1,000-fold. The method can include sequencing each strand 440. In some embodiments, the method includes comparing the sequences of two complementary strands to each other 450. In some embodiments, the method includes comparing the sequences of the complementary strands to a reference sequence 460. In some embodiments, the entire method is performed in a single microfluidic device. In some embodiments, the method is performed in a single microfluidic device up through the amplification 430, at which point the strands of nucleic acid are removed from the microfluidic device and used to construct sequencing libraries. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The skilled artisan will recognize that a variety of techniques can be used to separate nucleic acids from the cell according to embodiments herein. In some embodiments, the cell is lysed, for example via a freeze-thaw cycle (e.g. in liquid nitrogen), contacting the cell with an alkaline solution (e.g. potassium hydroxide, sodium hydroxide, or another suitable strong alkaline solution), or contacting the cell with a salt solution such as N-lauroylsarcosine salt.

In some embodiments, placing the first strands of the plurality of double-stranded nucleic acid (e.g. chromosomes) in a plurality of solutions comprises separating the strands and distributing the strands among the plurality of solutions. The strands can be distributed by a variety of approaches, for example mechanical rotation or passive diffusion. A variety of methods can be used for separating the strands, for example alkaline denaturation, or heat denaturation. As such, in some embodiments, alkaline solution is used to both isolate nucleic acids from cells, and separate the strands of nucleic acids.

In some embodiments, the strands are distributed by separating the complementary strands from each other, and then gently rotating the strands mechanically. Without being limited by any particular theory, gentle mechanical rotation can minimize shearing of single-stranded polynucleotides. Gentle mechanical rotation can be performed in a rotary member. In some embodiments mixing involves opening and closing multiple valves in fluid communication with the rotary member. In some embodiments, the rotary member comprises a ring. In some embodiments, the strands are separated from each other, and then placed in the rotary member. In some embodiments, the strands are placed in the rotary member, and then separated from each other. Following mechanical rotation, the strands can be distributed among a plurality of solutions.

In some embodiments, the strands are distributed by separating the complementary strands from each other, and then passively diffusing the strands into a plurality of solutions. In some embodiments, the strands are placed in a passive diffuser which comprises a passive diffusion membrane in fluid communication with the plurality of solutions. In some embodiments, the strands are first separated from each other, and then placed in the passive diffuser. In some embodiments, the strands are placed in the passive diffuser, and then separated from each other prior to diffusing into the plurality of solutions.

By distributing the strands among a plurality of different solutions, there can be a very high probability that for each chromosome (or other double-stranded polynucleotide), the complementary nucleic acids are in separate solutions. In some embodiments, there is at least a 95% probability that for each chromosome, the complementary nucleic acids are in separate solutions, for example about 95.1%, 96%, 97%, 98%, 99%, 99.5%, 99.9%, or 99.99%. The probability that complementary strands for all of the double-stranded polynucleotides are in separate solutions can depend upon the number of different double-stranded polynucleotides, which can be affected by the number of chromosomes in the single cell and the ploidy of the single cell, and as such, the number of different solutions needed to provide particular probability can differ. It is noted that in general, the lower the total number of chromosomes (or double stranded nucleic acids) om the single cell, the higher the probability that the strands will be distributed such that the complementary nucleic acids are in separate solutions. In some embodiments, 24 different solutions provide for a greater than 95% probability that no two strands of the same double-stranded polynucleotide are in the same solution. 24 different solutions can ensure this at least 95% probability for diploid human genomes (23 chromosome pairs) and diploid mouse genomes (19 chromosome pairs), noting that since a diploid mouse has fewer chromosomes than a diploid human, for diploid mouse, the probability will be slightly higher than for diploid human. In some embodiments, there are at least 10 different solutions, for example 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 different solutions. In some embodiments, the different solutions are positioned in a microfluidic device. In some embodiments, the different solutions are in fluid communications with the member as described herein.

In some embodiments, each of the plurality of solutions has a volume of 4 nl or less, for example about 4 nl, 3.5 nl, 3 nl, 2.5 nl, 2 nl, 1.5 nl, 1 nl, 0.5 nl, 0.4 nl, 0.3 nl, 0.2 nl, 0.1 nl, 0.09 nl, 0.05 nl, and 0.01 nl including ranges between any two of the listed values. In some embodiments, each of the plurality of solutions has a volume of 2 nl or less. In some embodiments, each of the plurality of solutions has a volume of 1 nl or less. In some embodiments, each of the plurality of solutions has a volume of 0.4 nl or less.

In some embodiments, the sequencing comprises amplifying each strand in the solution. In some embodiments, the amplification comprises multiple displacement amplification. Without being limited by any particular theory, it has been observed herein that amplification of each strand of about 1000-fold or less yields very uniform amplification along each nucleic acid (see, e.g. FIGS. 1 and 3). Moreover, without being limited by any particular theory, while 1000-fold amplification yields very uniform amplification for relatively large genomes such as human and mouse, it is contemplated herein that for smaller genomes uniformity can be obtained with substantially higher-fold amplification. As such, in some embodiments, each strand is amplified no more than about 10,000-fold, for example, no more than about 10,000-fold, 9000-fold, 8000-fold, 7000-fold, 6000-fold, 5000-fold, 4000-fold, 3000-fold, 2000-fold, 1500-fold, 1400-fold, 1300-fold, 1200-fold, 1100-fold, 1000-fold, 950-fold, 900-fold, 850-fold, 800-fold, 750-fold, 700-fold, 650-fold, 600-fold, 550-fold, 500-fold, 450-fold, 400-fold, 350-fold, 300-fold, 250-fold, 200-fold, 150-fold, or 100-fold. In some embodiments, sequencing comprises amplifying each strand about 100-fold to 1000-fold, about 200-fold to 1000-fold, about 300-fold to 1000-fold, about 400-fold to 1000-fold, about 500-fold to 1000-fold, about 600-fold to 1000-fold, about 700-fold to 1000-fold, about 800-fold to 1000-fold, about 900-fold to 1000-fold, about 950-fold to 1000-fold, about 100-fold to 900-fold, about 200-fold to 900-fold, about 300-fold to 900-fold, about 400-fold to 900-fold, about 500-fold to 900-fold, about 600-fold to 900-fold, about 700-fold to 900-fold, about 800-fold to 900-fold, about 100-fold to 800-fold, about 200-fold to 800-fold, about 300-fold to 800-fold, about 400-fold to 800-fold, about 500-fold to 800-fold, about 600-fold to 800-fold, or about 700-fold to 800-fold.

A desired fold-amplification can be achieved via a variety of approaches, for example reaction volume, selection of reagents, concentration of reagents, reaction conditions (such as temperature and the like), and reaction time. In some embodiments, reaction time is used to control the fold amplification. In some embodiments, each strand is amplified for no more than 24 hours, for example about 24 hours, 23, 22, 21, 20, 19, 18, 17, 16, 15, 14, 13, 12, 11, 10, 9, 8, 7, 6, 5, 4, 3, 2, or 1 hour. For many applications (e.g. for many genome sizes), amplification for no more than 5 hours can be suitable, but the skilled artisan will appreciate that this can depend on other factors as described herein. In some embodiments, each strand is amplified for no more than 5 hours. In some embodiments, each strand is amplified for no more than 3 hours.

A variety of amplification techniques can be used in accordance with embodiments herein. In some embodiments, multiple strand displacement is used. Multiple strand displacement can be performed under isothermal conditions, for example at about 30° C. Exemplary enzymes that can be used in multiple strand displacement include Φ29 DNA polymerase, and the large fragment of Bst polyemerase. Without being limited by any particular theory, template nucleic acids can be contacted with multiple random primers (typically hexamers, but in some embodiments, pentamers, heptamers, octamers, and the like can also be suitable), which can be extended by the polymerase, resulting in a branch network with multiple strands. The network can be debranched by contacting the network with nicking nucleases (e.g. S1 nucleases). Nicks in the product can then be repaired with a polymerase, for example DNA polymerase I. In some embodiments, thermal amplification, for example thermal cycling using a heat-stable polymerase such as Taq, is used. Repeated cycles of annealing primers to the template nucleic acids, extending the primers, and denaturing resultant double-stranded polynucleotides can be performed to provide multiple copies of nucleic acid. In some embodiments, the primers are random. In some embodiments, the primers are non-random.

A variety of techniques can be used to sequence each strand in solution. In some embodiments, the sequencing includes amplification of each strand, for example Illumina™ sequencing, IonTorrent™ sequencing, or the like. In some embodiments, the sequencing is multiplex. In some embodiments, the sequencing monitors base incorporation (including, for example, incorporation of base analogs) in single molecules. In some embodiments, the sequencing monitors incorporation of a fluorescently-labeled reversible terminator, so as to permit nucleotides to be added one-at-a-time, the base to be called, and flurophore cleaved to permit incorporation of the next fluorescently-labeled reversible terminator. In some embodiments, the strands are sequenced in the same microfluidic device that includes the member. In some embodiments, the strands are amplified in the microfluidic device, and amplicons are removed from the microfluidic device and subsequently used to make sequencing libraries. In some embodiments, the amplicons are removed from the microfluidic device by micromanipulation.

In some embodiments, the error rate of sequencing is about the square of the error rate of in vitro sequencing for a single strand. As an in vitro sequencing error will only be missed if the same error occurs at the same position on both strands. Accordingly, assuming no bias, the probability that an error will occur for a particular base and its complement is approximately the square of the in vitro sequencing error rate. For example, if the error rate for an individual strand is $10^{-6}$, the probability that an error will occur at the same position on both strands is $10^{-6} \times 10^{-16} = 10^{-12}$. Moreover, even if an in vitro sequencing error occurs at the same position on both strands, two-thirds of random errors in nucleotide sequencing will result in a mismatched base pairings that can detected and recognized as error (e.g. assuming a particular position has the base pair A-T, a random error on the first strand could be G, C, or T, and an error on the second strand could be A, G, or C; as such, while three possible pairings or erroneous bases may go undetected, G-C, C-G, or T-A, the remaining six possible pairings, G-A, G-G, C-A, C-C, T-G, or T-C would be identifiable as errors). As such, in some embodiments, the error rate is about two thirds of the square of the in vitro sequencing error rate for a single strand. In some embodiments, the sequencing error rate when both strands are sequenced is less than $10^{-9}$, for example about $10^{-9}$, $10^{-10}$, $10^{-11}$, $10^{-12}$, $10^{-13}$, $10^{-14}$, or $10^{-15}$, about $10^{-9}$ to about $10^{-15}$, about $10^{-9}$ to about $10^{-14}$, about $10^{-9}$ to about $10^{-13}$, about $10^{-9}$ to about $10^{-12}$, about $10^{-9}$ to about $10^{-11}$, about $10^{-9}$ to about $10^{-10}$, about $10^{-10}$ to about $10^{-15}$, about $10^{-10}$ to about $10^{-14}$, about $10^{-10}$ to about $10^{-13}$, about $10^{-10}$ to about $10^{-12}$, about $10^{-10}$ to about $10^{-11}$, about $10^{-11}$ to about $10^{-15}$, about $10^{-11}$ to about $10^{-14}$, about $10^{-11}$ to about $10^{-13}$, about $10^{-11}$ to about $10^{-12}$, about $10^{-12}$ to about $10^{-15}$, about $10^{-12}$ to about $10^{-14}$, about $10^{-12}$ to about $10^{-13}$, about $10^{-13}$ to about $10^{-15}$, about $10^{-13}$ to about $10^{-14}$, or about $10^{-14}$ to about $10^{-15}$. In some embodiments, the error rate is less than about $10^{-12}$.

Microfluidic Devices

In some embodiments, microfluidic devices for sequencing nucleic acids are provided. The device can comprise a single-cell capture module. The device can comprise a member configured for cell lysis and nucleic acid strand partitioning, for example a rotary member or passive diffuser. The device can comprise a plurality of chambers. The single-cell capture module can be in fluid communication with the member. The member can be in fluid communication with the plurality of reaction chambers. The device can be configured to distribute a plurality of partitioned single-stranded nucleic acids substantially evenly among the plurality of chambers.

FIG. 1A is a schematic diagram illustrating an exemplary microfluidic device 100 according to some embodiments herein. The device 100 can include a single-cell capture chamber 110, a member configured for cell lysis and nucleic acid strand partitioning 120 (for example a rotary member or passive diffuser), and a plurality of reaction chambers 130, for example 24. In some embodiments, the member 120 lyses single cells and mixes nucleic acids. In some embodiments, the member 120 lyses single cells and distributes nucleic acids. In some embodiments, the member 120 is connected to the single-cell capture module 110. The member 120 can be in fluid communication with the single-cell capture module 110. In some embodiments, the member 120 is connected to each of the reaction chambers 130. The member 120 can be in fluid communication with the reaction chambers 130. In some embodiments, the member 120 is directly connected to each of the reaction chambers 130. In some embodiments, the member 120 is connected to each of the reaction chambers 130 via a channel. In some embodiments, the member 120 is directly connected to each of the reaction chambers 130 and/or single-cell capture module 110. As such, the single-cell capture module 110, member 120, and reaction chambers 130 are all in fluid communication with each other. In some embodiments, each reaction chamber is in fluid communication with an output 140, for example an outlet valve.

Figure 1B:
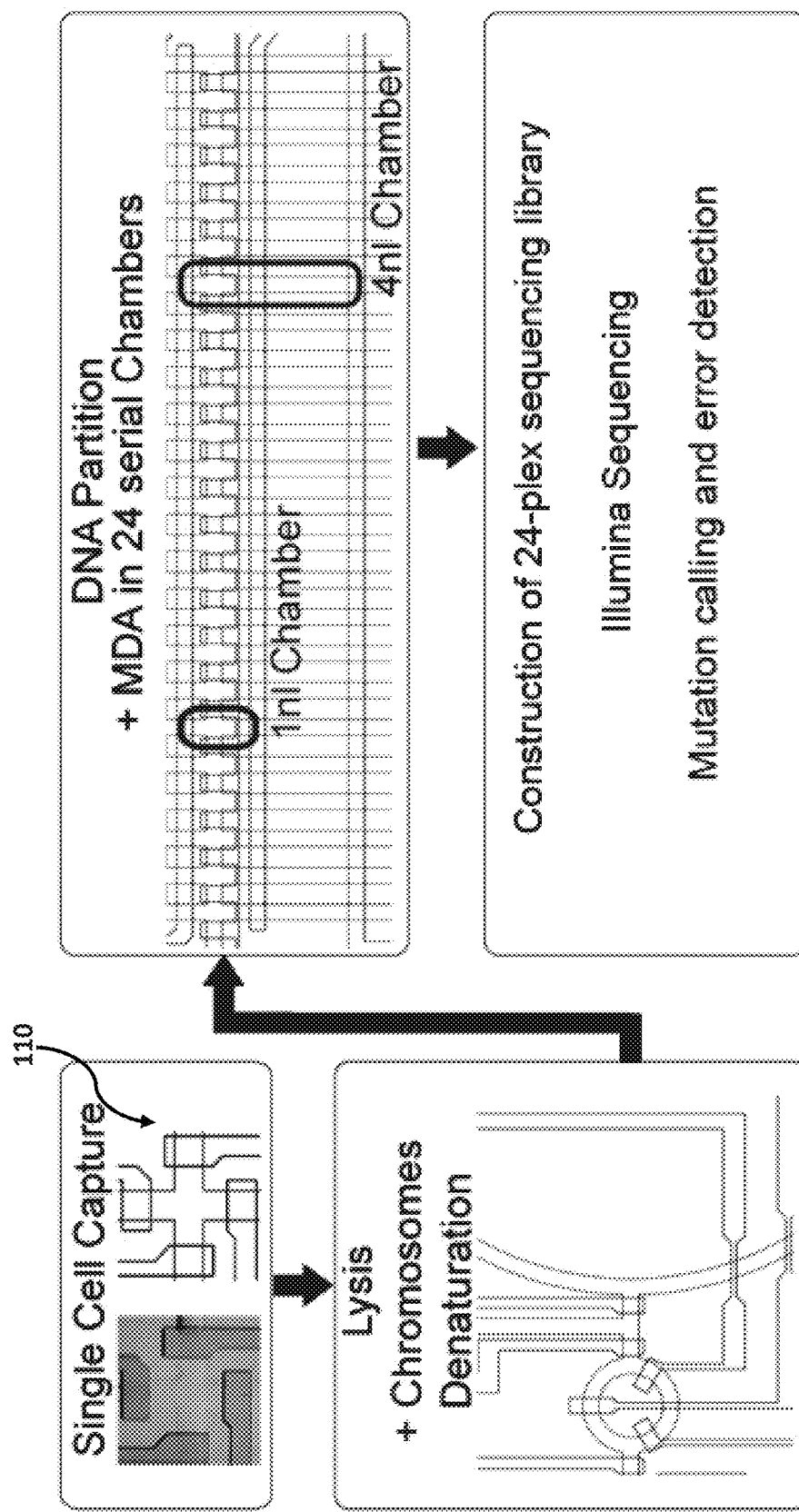
FIG. 1B is a schematic diagram of three modules for single-cell capture, partitioning, and amplification according to some embodiments herein

With reference to FIG. 1B, a single cell for subsequent extraction and analysis of polynucleotides can be positioned in the device. The single-cell capture module 110 of the device can be configured to move one cell in solution to the member 120. In some embodiments, the single-cell capture module is in fluid communication with the member 120. In some embodiments, the single-cell capture module 120 is in fluid communication with an input port for adding sample comprising one or more single cells to the microfluidic device. In some embodiments, the single-cell capture module 110 comprises at least one constriction, so that no more than one cell can fit through the constriction at a time. In some embodiments, the single-cell capture module 110 comprises at least two intersecting channels, wherein the intersection includes a constriction so that no more than one cell can pass between the channels at a time. An exemplary single-cell capture module 110 is illustrated in FIG. 1B.

Figure 1C:
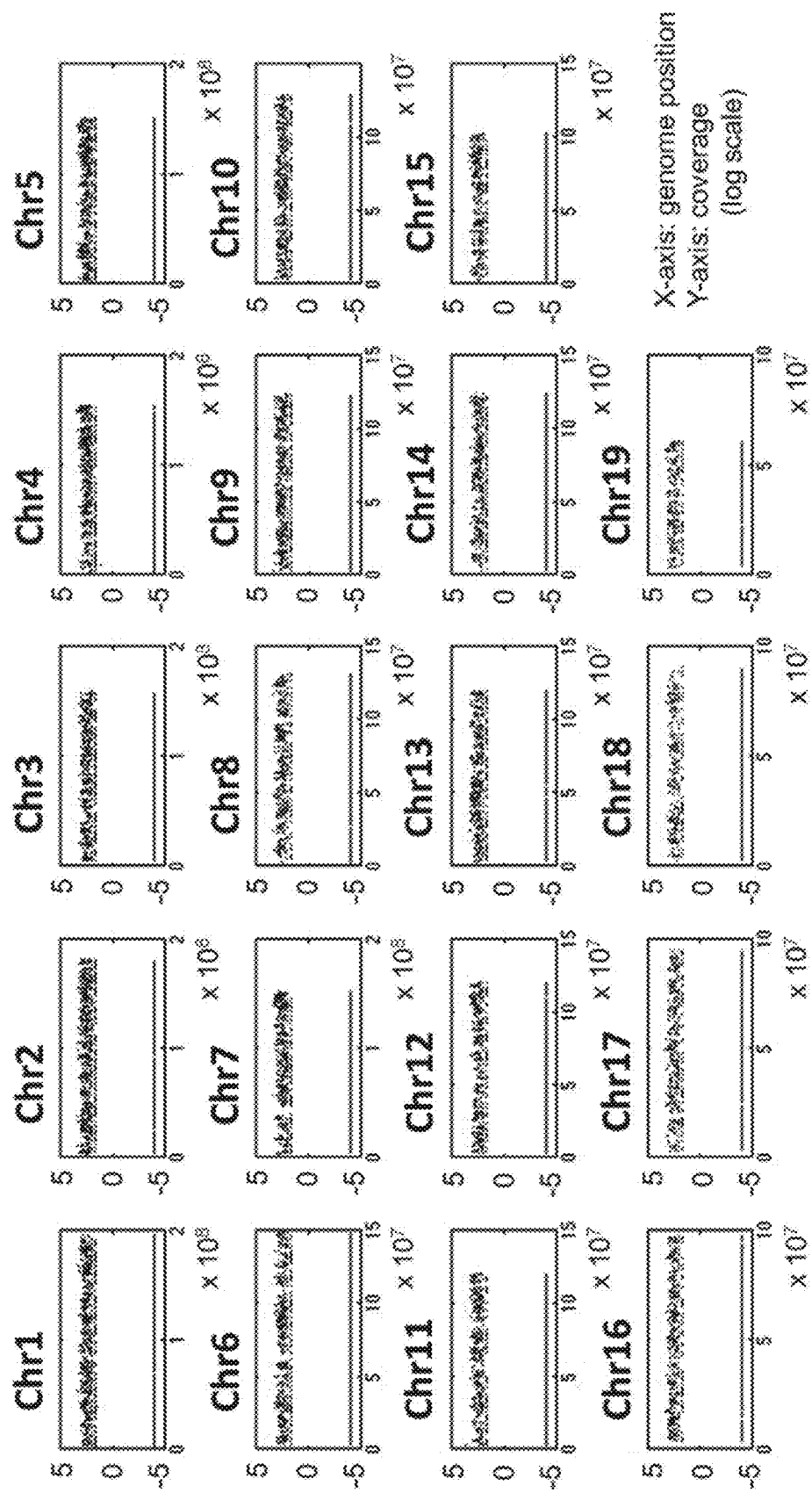
FIG. 1C is a series of graphs illustrating read depth distribution of single mouse embryonic fibroblast processed with the device schematically illustrated in FIG. 1A.
Figure 1D:
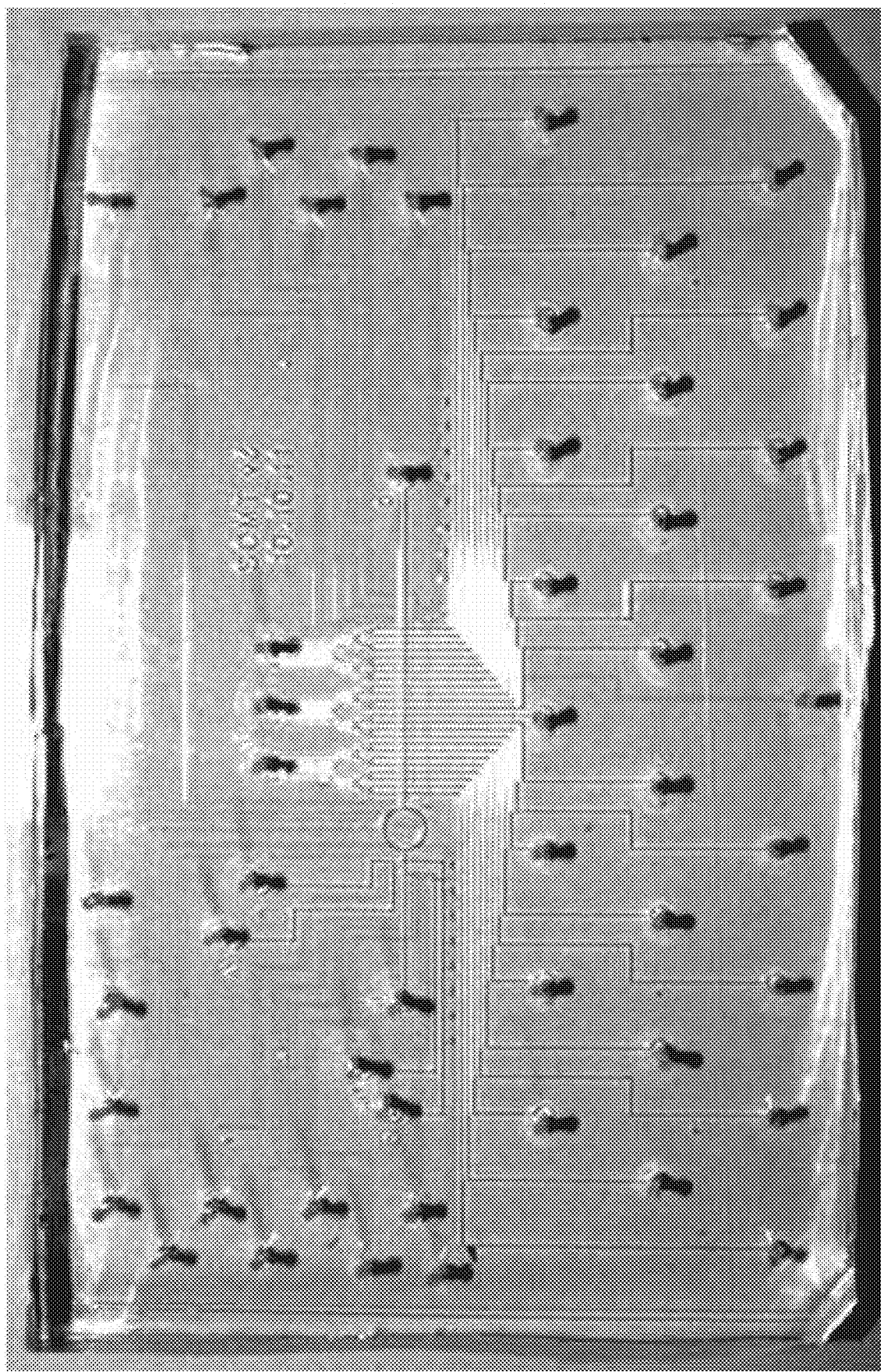
FIG. 1D is a photograph illustrating a device corresponding to the schematic diagram of FIG. 1A.

A photograph of an exemplary microfluidic device according to some embodiments herein is shown in FIG. 1D. Embodiments of the device described herein facilitate the precise control of the mixing and partitioning of DNA molecules with minimal non-specific binding. In some embodiments, the device employs a member, such as a rotary member, that allows complete denaturation of chromosomes and even distribution of single-stranded DNA molecules to 24 amplification chambers for independent amplification. This can ensure at least about a >95% probability that two complementary DNA strands are loaded in two separate chambers. In addition, just-enough amplification, is implemented to minimize the amplification bias from single cells. In some embodiments, the member comprises a passive diffusion membrane.

Figure 2A:
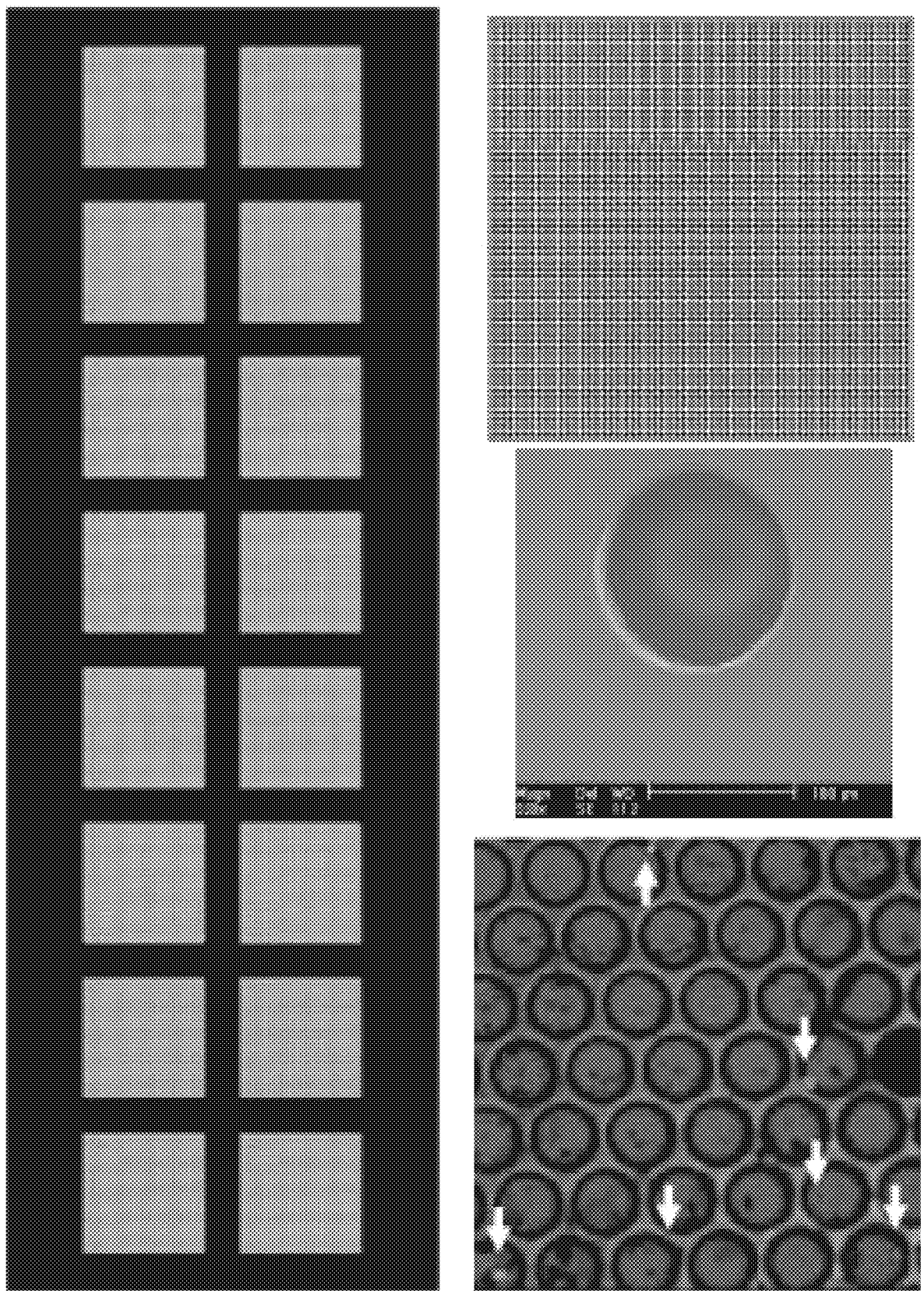
FIG. 2A is a series of photographs illustrating design of microwell arrays according to some embodiments herein. Each illustrated well is 100 µm in diameter.
Figure 2B:
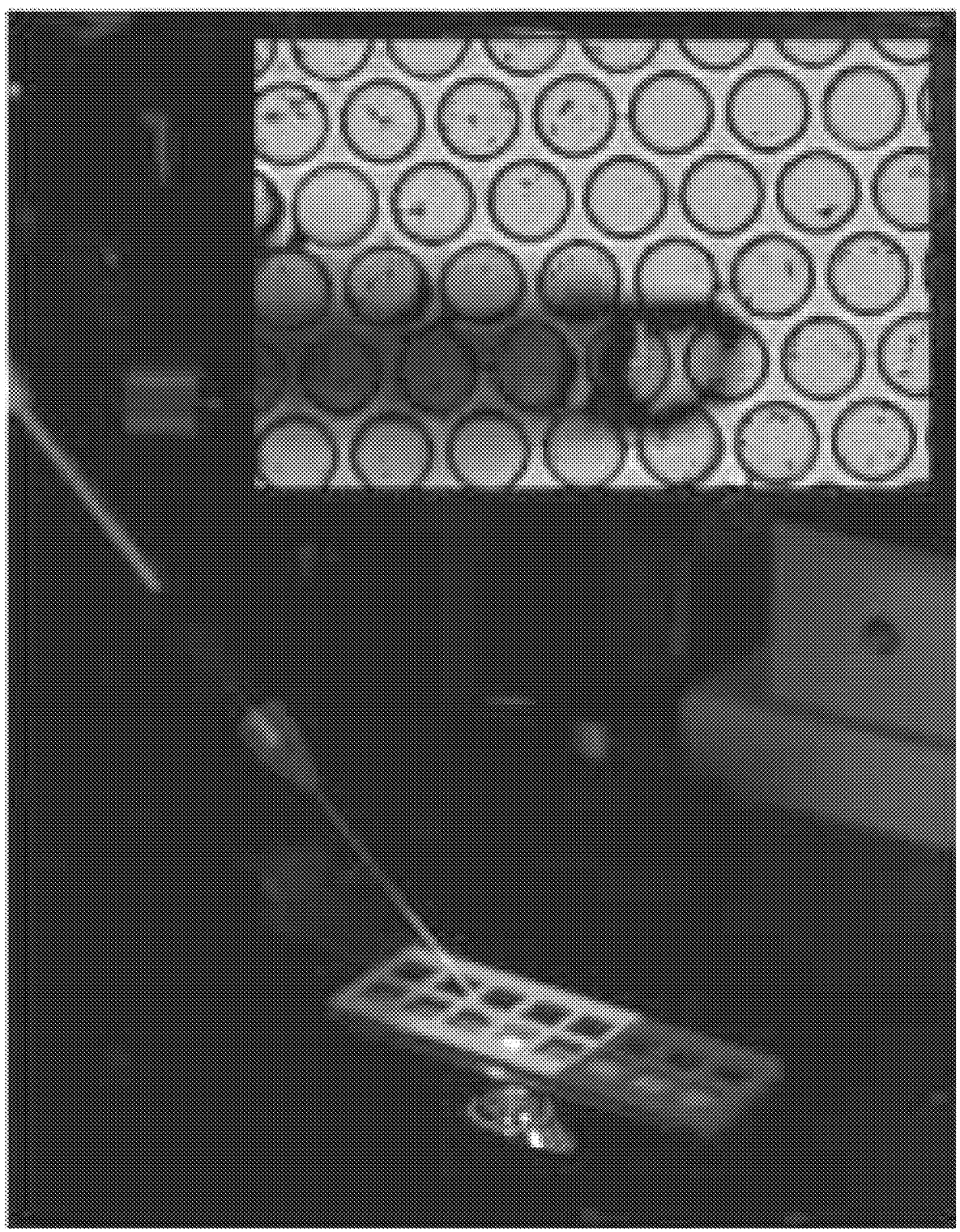
FIG. 2B is a series of photographs illustrating extraction of the amplicon of a single *E. coli* cell through micromanipulation according to some embodiments herein.
Figure 2C:
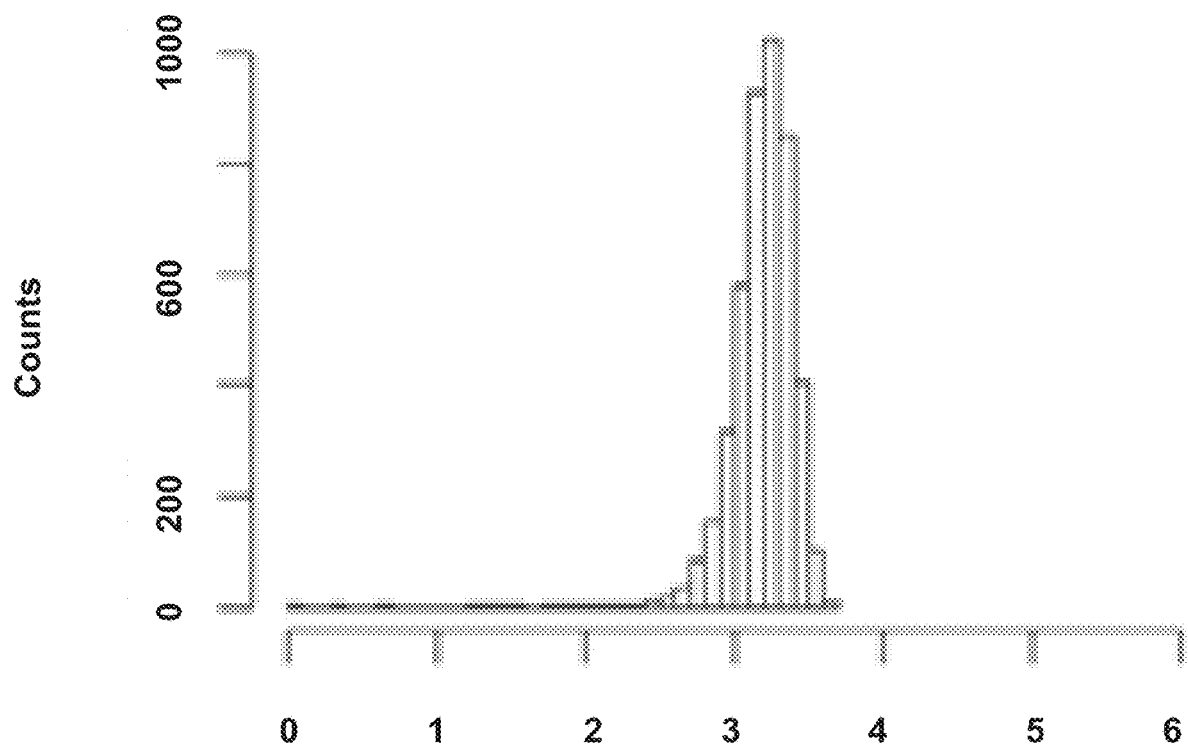
FIG. 2C is a graph illustrating log read depth distribution of a single *E. coli* sequencing library obtained according to some embodiments herein. The uniformity was dramatically improved with the combination of limited amplification and a novel library preparation method described herein.
Figure 2D:
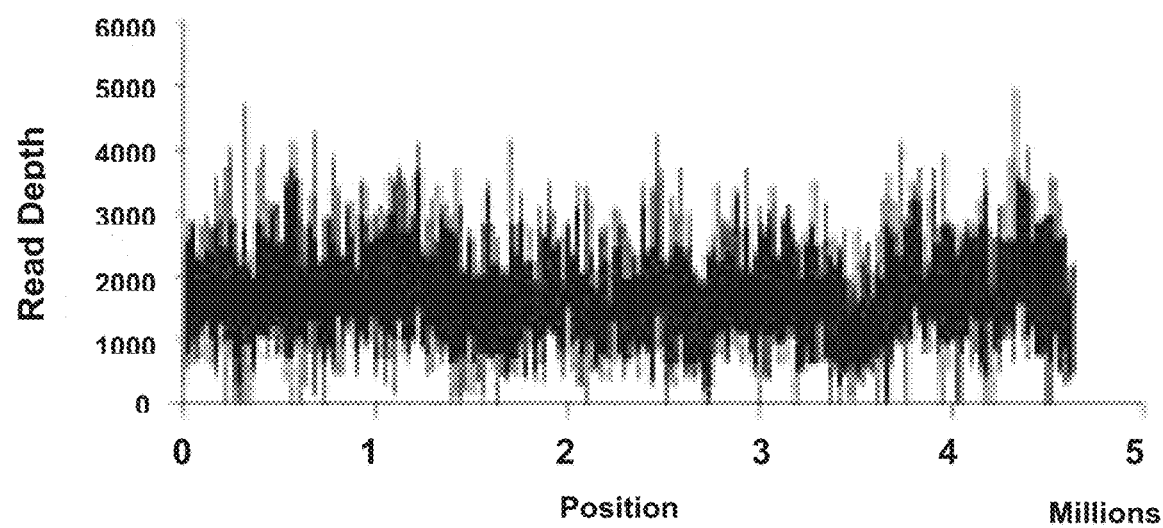
FIG. 2D is a graph illustrating read depth distribution of a single *E. coli* sequencing library obtained according to some embodiments herein. The uniformity was dramatically improved with the combination of limited amplification and a novel library preparation method described herein.

Separated strands of nucleic acid in solution can be distributed among the chambers in solution. In some embodiments, the strands can be amplified in the chambers. In some embodiments the device has 24 chambers. In some embodiments the device has at least 24 chambers. In some embodiments the device has at least 48 chambers. In some embodiments, the device has at least 10 chambers, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 chambers, including ranges between any two of the listed values. In some embodiments, the device has 20-30 chambers, 20-40 chambers, 25-30 chambers, 25-40 chambers, 15-25 chambers, 15-30 chambers, or 15-40 chambers. In some embodiments, each of the chambers is in fluid communication with the member. In some embodiments, each of the chambers is in fluid communication with the member via a channel connecting the member to each chamber. In some embodiments, each of the chambers has a volume of 4 nl or less, for example about 4 nl, 3.5 nl, 3 nl, 2.5 nl, 2 nl, 1.5 nl, 1 nl, 0.5 nl, 0.4 nl, 0.3 nl, 0.2 nl, and 0.1 nl, including ranges between any two of the listed values. In some embodiments, each of the chambers has a diameter of about 100 μm. In some embodiments, each of the chambers has a diameter of about 50 μm to 150 μm, 50 μm to 200 μm, 100 μm to 150 μm, or 100 μm to 200 μm. Exemplary chamber according to some embodiments herein are illustrated in FIG. 2A.

It can be helpful to minimize sticking of nucleic acids, cells, cell debris, and the like to the device. As such, in some embodiments, an inner surface of the device is coated with a non-stick polymer. In some embodiments, the non-stick polymer comprises polyethylene glycol (PEG). In some embodiments, the non-stick polymer comprises polyfluortetraethylene (PTFE).

In some embodiments, each of the plurality of chambers is configured for multiple-displacement amplification. In some embodiments, each chamber is configured for amplification under isothermal conditions. In some embodiments, the isothermal conditions comprise about 30° C. In some embodiments, the chambers comprise reagents for multiple displacement amplification, for example a polymerase such as Φ29 DNA polymerase, random primers (e.g. hexamer primers, heptamer primers, octamer primers, and the like), and/or nucleotide triphosphates. In some embodiments, the device include a heating element, a cooling element, or both of these to maintain isothermal conditions. In some embodiments, isothermal conditions can be maintained by controlling the ambient temperature of the device.

In some embodiments, the microfluidic device is configured to automatically capture a single cell, lyse the cell, and substantially evenly distribute single-stranded nucleic acids of the cell to the plurality of chambers. The operation of the microfluidic device can be under the control of a computer processor.

In some embodiments, each of the plurality of chambers is configured to transfer a quantity of fluid to a reaction vessel for sequencing library preparation. Each chamber can be in fluid communication with an exit port. In some embodiments, each chamber is in fluid communication with a different exit port. In some embodiments, two or more chambers are in fluid communication with the same exit port, and the contents of each chamber can be expelled separately (e.g. serially) into different reaction vessels for sequencing. In some embodiments, the contents of each chamber (e.g. amplicons) can be removed by micromanipulation.

In some embodiments, SISSOR is implemented in a microfluidic device that has three functional modules for cell capture, lysis and single-strand DNA partitioning, and single-molecule whole genome amplification. In some embodiments, SISSOR facilitates the precise control (mixing, partitioning) of DNA molecules in the device with minimal non-specific binding. Furthermore, in some embodiments the method is implemented with "just-enough amplification", so as to minimize amplification bias from single cells. In some embodiments, "just enough amplification" comprises no more than about 1000-fold amplification.

Some embodiments include a device (FIGS. 1 A&B). In some embodiments a member, such as rotary member (e.g. a ring), which allows completely denaturing the chromosomes and evenly distribute single-stranded DNA molecules to 24 amplification chambers for independent amplification is utilized. This can ensure a >95% probability that two complementary DNA strands are loaded in two separate chambers. To construct DNA sequencing libraries from individual DNA strands, multiple-displacement amplification (MDA) can be performed in a nanoliter volume, roughly 10× smaller than the 50 nl volume implemented by Marcy et al. 2007. In some embodiments of the present methods, amplification is performed in a volume of about 12 nl or less, for example about 12 nl, 10 nl, 5 nl, 3 nl, 2 nl, 1 nl, or 0.5 nl. Additionally, in some embodiments the amplification time is limited to about 10 hours or less, for example about 10 hours or less, about 5-10 hours, about 5-7 hours, about 7 hours or less, about 5 hours or less, about 3-5 hours, or about 3 hours or less. In some embodiments, this combination of low volumes and relatively short amplification yields a magnitude of amplification of about 1000-fold or less, which can achieve a very uniform amplification based using a type of nanoreactor, as shown in FIG. 2.#

High shearing force can cause DNA fragmentation. Thus, in some embodiments, the member is optimized to minimize DNA fragmentation. In some embodiments, the member comprises a rotary member such as a mixing ring configured for gentle mixing. In some embodiments, the member comprises a passive diffuser, which can comprise a passive diffusion membrane. While unbiased amplification has been demonstrated herein, some embodiments include additional modifications to the methods and/or devices. Even and random partitioning of long single-strand DNA molecules can distinguish true mutations from false positives. In some embodiments, the rotary element (e.g. a mixing ring) and amplification chambers ensure evenness and/or randomness of the partitioning. In some embodiments, inner surfaces of the device are coated with non-stick polymers (such as PEGs) to prevent non-specific DNA binding. In some embodiments, the geometry of the channels and chambers is be optimized to avoid dead volume. In some embodiments, genome sequencing libraries are constructed from nanogram level of MDA amplicons.

Some embodiments include a protocol based on DNA polymerase I debranching and Tn-5 transposon tagmentation. This protocol is >10× more efficient than published methods and yields sequencing libraries with >10× higher complexity. In some embodiments, there is one sequencing library for each chamber, so that a single cell yields a number of sequencing libraries equal to the number of chambers (e.g. if there are 24 chambers, there can be 24 sequencing libraries). Thus, the scale of the experiment can grow quickly as more single cells are sequenced. As such, in some embodiments, this library preparation protocol is automated using a liquid handling robot to ensure that every single amplicon eluted off the microfluidic device is converted into a sequencing library consistently.

Exemplary applications of some embodiments herein include early detection of rare mutations in cancers, and other genetic diagnostic applications that involve very limited input materials and require highly accurate sequencing.

In some embodiments, a method and/or apparatus for highly accurate genome sequencing of single mammalian cells will represent a major technical advance by itself. In some embodiments, this technology is applied to characterizing the somatic genome diversity of single neurons in adult human brain, which is a barely explored area and might lead to a paradigm shift in our understanding of the functional diversity of neurons in adult brain and brain disorders.

Example 1: Library Preparation

Low-input library preparation method started with preparing an MDA amplicon that was flushed out from amicrofluidic device in 1 ul. First, hyper-branched MDA amplicons were converted into double-stranded blunt-ended DNA. For this, 1.5 ul of alkaline denaturization buffer (400 mM KOH, 100 mM DTT, 10 mM EDTA) were added to the 1 ul MDA amplicon, and the reaction was incubated at room temperature for 3 minutes, and transferred onto ice. The reaction was neutralized with 1.5 ul of neutralization solution (400 mM HCl, 600 mM Tris.HCl, pH 7.5). 2 ul 10×DNA polymerase I buffer, 1 ul 10 mM dNTP, 5 ul 20 uM random hexamer, 7 ul nuclease-free H2O, and 1 ul DNA polymerase I (10 U/ul) were then added. The reaction was incubated at 37 C for 1 hour, and inactivated at 65 C for 10 minutes. The resulting double-stranded blunt-ended DNA was purified by ethanol precipitation, and resuspended in 10 ul H2O.

Next the double-stranded blunt-ended DNA was converted into Illumina sequencing libraries by Nextera tagmentation (Epicentre). Briefly, 7 ul of DNA with 2 ul of 5×HMW buffer (Epicentre Nextera kit), and 1:50 diluted transposase (Epicentre Nextera kit) were mixed and incubated the reaction at 55 C for 5 minutes. Then, 1 ul 1:100 diluted protease (Qiagen) was added, and the reaction was incubated at 50 C for 10 minutes, and 70 C for 20 minutes. Next, 1 ul exo-klenow fragment (10 U/ul, NEB) and 1 ul 10 mM dNTP, were added and incubated at 37 C for 15 minutes. The resulting tagmented DNA (13 ul) was PCR amplified in 50 ul of 1×KAPA Robust PCR master mix with 200 nM of Nextera primer cocktail and 0.4× Sybr Green I using the thermalcycling protocol: 95 C for 30 seconds, followed by 15 cycles of 95 C for 10 seconds, 62 C for 15 seconds and 72 C for 2 minutes. The reaction was monitored on a real-time thermalcycler, and terminated when the amplification curve just approached the plateau. The resulting PCR amplicon was purified with Agencourt AmPure magnetic beads and submitted for sequencing.

Example 2: Sequencing of the Genome of a Single Mouse Fibroblast

An experiment successfully was performed on a single mouse embryonic fibroblast using a prototype device as described herein in FIG. 1B. The protocol described in Example 1 was performed. The protocol achieved a fairly even amplification across the entire mouse genome (FIG. 1C).

Example 3: Characterization of Somatic Genomic Diversity in Human Adult Brains and in vitro Differentiated Neurons Characterization of somatic genomic diversity in human adult brains and in vitro differentiated neurons. Accumulating evidences suggest the presence of genomic mosaicism in human adult brain, and that it could be specific to cell types, brain functional areas and even status of certain brain disorders. Using the SISSOR technology the extent of genomic diversity (both single-nucleotide changes and copy number changes of large regions) are characterized in human post-mortem brains.

The somatic genomic diversity at single-nucleotide resolution is comprehensively characterized on individual neurons in human post-mortem brains. One focus is neurons in the prefrontal cortex, because of existing evidence that such neurons tend to exhibit gains of total DNA content. Westra, J. W., et al. (2010) "Neuronal DNA content variation (DVC) with regional and individual differences in the human brain. *J Comp Neurol* 518: 3981-4000, the disclosure of which is incorporated by reference in its entirety herein. Neurons are highly and tightly inter-connected in adult brains. Applicants are not aware of a previous technology that permits isolating single intact neuron from post-mortem brain sections. Neuronal nuclei are specifically isolated for SCISSOR, using a combination of immuno-staining, micro-dissection and flow sorting. Briefly, laser capture is performed on brain sections of ~20 µm thick to harvest ~10,000 cells from specific layers (i.e. Layer IVc), in which one particular neuronal cell type (i.e. stellate interneurons) is easily identifiable and dominating. The captured cells are gently lysed, stained with NeuN antibody to specifically label neuronal nuclei, and flow-sorted. Individual NeuN+ nuclei will be loaded to our microfluidic chip for DNA strand separation, partition and amplification. Mutation calling is performed on each sequencing library first, the candidate mutations from all 24 genomic subsets are combined to identify true mutations. Depth of coverage for the 24 data sets will also be combined for the identification of gains or losses of large genomic regions. Zhang, K., et al. (2006) "Sequencing genomes from single cells by polymerase cloning. *Nat. Biotechnol* 24: 680-686, the disclosure of which is incorporated by reference in its entirety herein. Glia nuclei (NeuN−) in the same cortex section and NeuN+ nuclei from cerebellum of the same brain are used as controls, based on existing evidence that these cells tend to have normal total DNA contents. It is expected that somatic genetic changes of both single nucleotides and large chromosomal fragments will be identified. This experiment may indicate (i) what is the frequency of somatic mutations in three types of single cells and the variability among different cells of the same types; (ii) what are the genomic locations of the mutations and whether there is any enrichment in terms of genomic locations, epigenetic status, genes or pathways; (iii) what fraction of mutations are shared among cells of different types or same types?

Example 4: Identification of the Origin of Somatic Genomic Changes

The origin of such somatic genomic changes is identified by examining the genome integrity of single cells during in vitro differentiation of neurons from human pluripotent stem cells.

The source(s) of somatic mutation are identified in individual neurons by analyzing neurons and neural progenitors differentiated from human pluripotent stem cells in vitro. Specifically, this approach can distinguish two hypotheses: (i) mutations are accumulated during in the process of neuronal differentiation and cell fate decision in the early stages of embryo development; (ii) mutations occur in post-mitotic adult neurons and might be directly or indirectly related to the functional neuronal activities. Exemplary protocols for in vitro differentiation of neural stem cells from human embryonic stem cells and episomal reprogrammed hiPS cells can be found in Yuan, S. H., et al. (2011) "Cell-surface marker signatures for the isolation of neural stem cells, glia and neurons derived from human pluripotent stem cells." *PLoS One* 6: e17540, and Israel et al. (2012) Probing sporadic and familial Alzheimer's disease using induced pluripotent stem cells. *Nature* 482: 216-220, each of which is incorporated by reference herein in its entirety. Using a live-cell imaging and micromanipulation system recently established in my group, cell tracking is performed, and individual cells are extracted. These individual cells are separated by defined numbers of cell divisions for single-cell whole genome sequencing. Under the first hypothesis, it is expected that shared mutations between cells are observed. Based on the degree of mutation sharing, a lineage tree consistent with the developmental hierarchy can be constructed. In addition, most mutations should occur at random locations with no significant functional enrichment. On the other hand if the second hypothesis is true, there should be few or no shared mutation among cells that are close to each other in the developmental lineage. If mutagenesis occurs in the post-mitotic neurons, observation of a significantly low level of mutation load in the in vitro differentiated resting neurons would be expected as, compared with neurons from post-mortem brains. Finally, if mutagenesis is activity related, enrichment of mutations in certain genomic regions or pathways might be observed for neurons in the same functional cortex area.

Example 5: Additional Sequencing of Normal Adult Brains and In Vitro Differentiated Neurons Additional sequencing is performed on normal adult brains and in vitro differentiated neurons. Brain specimens from patients of neurodegenerative diseases are studied. If certain genomic regions or pathways are commonly mutated in vivo, characterization of functional consequences can be performed in follow-up. Single-cell sequencing can be performed in situ, for example to map the somatic mutations to the three-dimensional anatomical structure of the brain.

Example 6: Genomic Sequencing of Single Human Fibroblast Cells

Human fibroblast cells were loaded to the microfluidic processor, and one single cell was trapped in the single-cell capture module. After washing, the cell was lysed with an alkaline buffer, and the cellular content was move to the rotary member, in which the double-stranded DNA of all chromosomes were dissociated through the combined effects of alkaline denaturation and gentle mechanic mixing (Note that in the V9 design this entire step was performed in the denature chamber without mechanic mixing to minimize DNA fragmentation). Large single-stranded DNA fragments were randomly partitioned into 24 lower compartments of 0.4 nL in volume, and mixed with a neutralization solution in each of the 24 upper compartments. The neutralized DNA solution in each compartment was then pushed to a MDA reaction chamber and mixed with the amplification reaction mix in a volume of 23 nL. Amplification was performed in 24 amplification chamber in parallel overnight, then the amplicons were flushed out and collected into individual 0.2 mL PCR tubes for constructing Illumina sequencing libraries (Note that in V9 design, one additional amplification was performed on the DNA molecules remained in the denature chamber. Hence a total of 25 amplicons were collected per single cell). Each amplicon was converted into a library labeled with a unique DNA barcode, and all 24 sequencing libraries were pooled for sequencing on Illumina GA IIx or HiSeq2500 sequencers. Sequencing reads were aligned to the human genome reference sequence following the BWA/GATK best practice V4. Aligned sequencing reads in bam files were visualized with SeqMonk. Representative results are shown in FIG. 3. It is noted that while the entire human genome was sequenced, only one representative 2.5 megabase region of chromosome 19 is shown in FIG. 3.

LIST OF REFERENCES

The following references are hereby incorporated by reference in their entirety for all purposes:

Existing methods for amplification and sequencing of single cells at the error rate of ~10-5. Lasken R S, Dean F B, Nelson J (2000) Multiply-primed amplification of nucleic acid sequences. U.S. Pat. No. 6,323,009

Zhang K, Martiny A C, Reppas N B, Barry K W, Malek J, Chisholm S W, Church G M. (2006) Sequencing genomes from single cells by polymerase cloning. Nature Biotechnology 24:680-686

Church G M, Zhang K (2006) US Patent Appl #2006/0014167 Amplification of trace amounts of nucleic acids.

Marcy Y, Ishoey T, Lasken R S, Stockwell T B, Walenz B P, Halpern A L, Beeson K Y, Goldberg S M, Quake S R. 2007.

Nanoliter reactors improve multiple displacement amplification of genomes from single cells. PLoS Genet 3(9): 1702-1708.

Xu X, Hou Y, Yin X, Bao L, Tang A, Song L, Li F, Tsang S, Wu K, Wu H et al. 2012. Single-cell exome sequencing reveals single-nucleotide mutation characteristics of a kidney tumor. Cell 148(5): 886-895.

Zhang K, Martiny A C, Reppas N B, Barry K W, Malek J, Chisholm S W, Church G M. (2006) Sequencing genomes from single cells by polymerase cloning. Nature Biotechnology 24:680-686

Marcy Y, Ishoey T, Lasken R S, Stockwell T B, Walenz B P, Halpern A L, Beeson K Y, Goldberg S M, Quake S R. 2007. Nanoliter reactors improve multiple displacement amplification of genomes from single cells. PLoS Genet 3(9): 1702-1708.

Xu X, Hou Y, Yin X, Bao L, Tang A, Song L, Li F, Tsang S, Wu K, Wu H et al. 2012. Single-cell exome sequencing reveals single-nucleotide mutation characteristics of a kidney tumor. Cell 148(5): 886-895.

Schmitt M W, Kennedy S R, Salk J J, Fox E J, Hiatt J B, Loeb L A. (2012) Detection of ultra-rare mutations by next generation sequencing. Proc Natl Acad Sci USA. 2012 doi: 10.1073/pnas.1208715109 [Epub ahead of print]

Gore, A., Li, Z., Fung, H. L., Young, J. E., Agarwal, S., Antosiewicz-Bourget, J., Canto, I., Giorgetti, A., Israel, M. A., Kiskinis, E., et al. (2011). Somatic coding mutations in human induced pluripotent stem cells. Nature 471, 63-67.

Rehen, S. K., Yung, Y. C., McCreight, M. P., Kaushal, D., Yang, A. H., Almeida, B. S., Kingsbury, M. A., Cabral, K. M., McConnell, M. J., Anliker, B., et al. (2005). Constitutional aneuploidy in the normal human brain. J Neurosci 25, 2176-2180.

Rehen, S. K., McConnell, M. J., Kaushal, D., Kingsbury, M. A., Yang, A. H., and Chun, J. (2001). Chromosomal variation in neurons of the developing and adult mammalian nervous system. Proc Natl Acad Sci USA 98, 13361-13366.

Yang, A. H., Kaushal, D., Rehen, S. K., Kriedt, K., Kingsbury, M. A., McConnell, M. J., and Chun, J. (2003). Chromosome segregation defects contribute to aneuploidy in normal neural progenitor cells. J Neurosci 23, 10454-10462.

Yurov, Y. B., Iourov, I. Y., Vorsanova, S. G., Liehr, T., Kolotii, A. D., Kutsev, S. I., Pellestor, F., Beresheva, A. K., Demidova, I. A., Kravets, V. S., et al. (2007). Aneuploidy and confined chromosomal mosaicism in the developing human brain. PLoS One 2, e558.

Muotri, A. R., and Gage, F. H. (2006). Generation of neuronal variability and complexity. Nature 441, 1087-1093.

Singer, T., McConnell, M. J., Marchetto, M. C., Coufal, N. G., and Gage, F. H. (2010). LINE-1 retrotransposons: mediators of somatic variation in neuronal genomes? Trends Neurosci 33, 345-354.

Westra, J. W., Rivera, R. R., Bushman, D. M., Yung, Y. C., Peterson, S. E., Barral, S., and Chun, J. (2010). Neuronal DNA content variation (DCV) with regional and individual differences in the human brain. J Comp Neurol 518, 3981-4000.

Luria, S. E., and Delbruck, M. (1943). Mutations of Bacteria from Virus Sensitivity to Virus Resistance. Genetics 28, 491-511.

Albertini, R. J., Nicklas, J. A., O'Neill, J. P., and Robison, S. H. (1990). In vivo somatic mutations in humans: measurement and analysis. Annu Rev Genet 24, 305-326.

Garcia, A. M., Busuttil, R. A., Rodriguez, A., Cabrera, C., Lundell, M., Dolle, M. E., and Vijg, J. (2007). Detection and analysis of somatic mutations at a lacZ reporter locus in higher organisms: application to Mus musculus and Drosophila melanogaster. Methods Mol Biol 371, 267-287.

Roach, J. C., Glusman, G., Smit, A. F., Huff, C. D., Hubley, R., Shannon, P. T., Rowen, L., Pant, K. P., Goodman, N., Bamshad, M., et al. (2010). Analysis of genetic inheritance in a family quartet by whole-genome sequencing. Science 328, 636-639.

Navin, N., Kendall, J., Troge, J., Andrews, P., Rodgers, L., McIndoo, J., Cook, K., Stepansky, A., Levy, D., Esposito, D., et al. (2011). Tumour evolution inferred by single-cell sequencing. Nature 472, 90-94.

Hou, Y., Song, L., Zhu, P., Zhang, B., Tao, Y., Xu, X., Li, F., Wu, K., Liang, J., Shao, D., et al. (2012). Single-cell exome sequencing and monoclonal evolution of a JAK2-negative myeloproliferative neoplasm. Cell 148, 873-885.

Xu, X., Hou, Y., Yin, X., Bao, L., Tang, A., Song, L., Li, F., Tsang, S., Wu, K., Wu, H., et al. (2012). Single-cell exome sequencing reveals single-nucleotide mutation characteristics of a kidney tumor. Cell 148, 886-895.

Marcy, Y., Ishoey, T., Lasken, R. S., Stockwell, T. B., Walenz, B. P., Halpern, A. L., Beeson, K. Y., Goldberg, S. M., and Quake, S. R. (2007). Nanoliter reactors improve multiple displacement amplification of genomes from single cells. PLoS Genet 3, 1702-1708.

Zhang, K., Martiny, A. C., Reppas, N. B., Barry, K. W., Malek, J., Chisholm, S. W., and Church, G. M. (2006). Sequencing genomes from single cells by polymerase cloning. Nat Biotechnol 24, 680-686.

Baslan, T., Kendall, J., Rodgers, L., Cox, H., Riggs, M., Stepansky, A., Troge, J., Ravi, K., Esposito, D., Lakshmi, B., et al. (2012). Genome-wide copy number analysis of single cells. Nat Protoc 7, 1024-1041.

Yuan, S. H., Martin, J., Elia, J., Flippin, J., Paramban, R. I., Hefferan, M. P., Vidal, J. G., Mu, Y., Killian, R. L., Israel, M. A., et al. (2011). Cell-surface marker signatures for the isolation of neural stem cells, glia and neurons derived from human pluripotent stem cells. PLoS One 6, e17540.

Israel, M. A., Yuan, S. H., Bardy, C., Reyna, S. M., Mu, Y., Herrera, C., Hefferan, M. P., Van Gorp, S., Nazor, K. L., Boscolo, F. S., et al. (2012). Probing sporadic and familial Alzheimer's disease using induced pluripotent stem cells. Nature 482, 216-220.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

While the present invention has been described in some detail for purposes of clarity and understanding, one skilled in the art will appreciate that various changes in form and detail can be made without departing from the true scope of the invention.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

What is claimed is:

1. A method of sequencing nucleic acid of a single cell, the method comprising:
isolating a plurality of double-stranded nucleic acids of a single cell, wherein each double-stranded nucleic acid of the plurality comprises a first strand of nucleic acid and a complementary second strand of nucleic acid, and wherein the first strand and the complementary second strand are complementary to each other;
denaturing the double-stranded nucleic acids to form a plurality of single strands;
randomly partitioning the plurality of single strands in a plurality of solutions, wherein the plurality of single strands are not bound to beads or other solid supports during the random partitioning, wherein each of the plurality of solutions is separate from each other solution, wherein there is at least a 95% probability that for each double-stranded nucleic acid, the first strand and complementary second strand are in separate solutions, and wherein the number of strands in each solution is substantially similar; and
sequencing each strand of the plurality of double-stranded nucleic acids.

2. The method of claim 1, wherein the double-stranded nucleic acids comprise double-stranded nucleic acids of at least one of chromosomes or chromosome fragments.

3. The method of claim 1, wherein each of the plurality of solutions has a volume of about 10 nl or less.

4. The method of claim 1, wherein each of the plurality of solutions has a volume of about 0.4 nl or less.

5. The method of claim 1, wherein each strand is amplified by multiple strand displacement amplification.

6. The method of claim 1, wherein sequencing each strand comprises amplifying nucleic acids for no more than about 24 hours.

7. The method of claim 1, wherein sequencing comprises an error rate of less than about 1 in $10^{10}$.

8. The method of claim 1, wherein the plurality of solutions is positioned in a microfluidic device.

9. The method of claim 1, wherein the probability is at least about 98% that for each double-stranded nucleic acid, the first strand and complementary second strand are in separate solutions.

10. The method of claim 1, further comprising amplifying each strand in the plurality of solutions by no more than 10,000-fold.

11. The method of claim 1, wherein the plurality of double-stranded nucleic acids or plurality of single strands are not amplified before randomly partitioning the plurality of single strands.

12. The method of claim 1, wherein the single strands have a length of at least 100 kilobases.

13. The method of claim 1, wherein the plurality of double-stranded nucleic acids or plurality of single strands are not amplified before randomly partitioning the plurality of single strands, and wherein the single-stranded nucleic acids have a length of at least 100 kilobases.

* * * * *